US011241285B2

(12) United States Patent
Viscardi et al.

(10) Patent No.: US 11,241,285 B2
(45) Date of Patent: Feb. 8, 2022

(54) ROBOTIC SYSTEM FOR SHOULDER ARTHROPLASTY USING STEMLESS IMPLANT COMPONENTS

(71) Applicant: MAKO Surgical Corp., Ft. Lauderdale, FL (US)

(72) Inventors: David Viscardi, Glen Rock, NJ (US); Jan Heinsohn, Hoboken, NJ (US); Andrew Nelson, New York City, NY (US); Phil Kemp, White Plains, NY (US); Rajan Yadav, New Delhi (IN); Jetinder Singh, Gurgaon (IN); Koustubh Rao, Gurgaon (IN)

(73) Assignee: MAKO Surgical Corp., Ft. Lauderdale, FL (US)

( * ) Notice: Subject to any disclaimer, the term of this patent is extended or adjusted under 35 U.S.C. 154(b) by 320 days.

(21) Appl. No.: 16/181,830

(22) Filed: Nov. 6, 2018

(65) Prior Publication Data

US 2019/0142518 A1 May 16, 2019

Related U.S. Application Data

(60) Provisional application No. 62/582,620, filed on Nov. 7, 2017.

(51) Int. Cl.
*A61B 34/10* (2016.01)
*A61F 2/40* (2006.01)
(Continued)

(52) U.S. Cl.
CPC .............. *A61B 34/10* (2016.02); *A61B 34/20* (2016.02); *A61B 34/30* (2016.02); *A61B 34/32* (2016.02);
(Continued)

(58) Field of Classification Search
CPC combination set(s) only.
See application file for complete search history.

(56) References Cited

U.S. PATENT DOCUMENTS

| 5,824,085 A | 10/1998 | Sahay et al. |
| 6,002,859 A | 12/1999 | DiGioia, III et al. |

(Continued)

FOREIGN PATENT DOCUMENTS

| EP | 0176711 A1 | 4/1986 |
| WO | 2009057964 A2 | 5/2009 |

(Continued)

OTHER PUBLICATIONS

Arthrex, Inc., "Partial Eclipse Stemless Shoulder Arthroplasty Brochure", 2016, 12 pages.

(Continued)

*Primary Examiner* — Andrew Yang
(74) *Attorney, Agent, or Firm* — Howard & Howard Attorneys PLLC

(57) ABSTRACT

Robotic systems and methods for robotic arthroplasty. The robotic system includes a machining station and a guidance station. The guidance station tracks movement of various objects in the operating room, such as a surgical tool, a humerus of a patient, and a scapula of the patient. The guidance station tracks these objects for purposes of controlling movement of the surgical tool relative to virtual cutting boundaries or other virtual objects associated with the humerus and scapula to facilitate preparation of bone to receive a shoulder implant system. In some versions, planning for placement of a stemless implant component is based on a future location of a stemmed shoulder implant to be placed in the humerus during a revision surgery.

16 Claims, 9 Drawing Sheets

(51) Int. Cl.
  *A61B 34/32*   (2016.01)
  *A61B 34/00*   (2016.01)
  *A61B 34/37*   (2016.01)
  *A61B 34/20*   (2016.01)
  *A61B 34/30*   (2016.01)
  *A61F 2/46*    (2006.01)
  *A61B 90/00*       (2016.01)
  *A61B 17/16*       (2006.01)
  *A61B 17/14*       (2006.01)
  *A61B 17/15*       (2006.01)
  *A61B 17/56*       (2006.01)
  *A61F 2/30*        (2006.01)

(52) U.S. Cl.
  CPC ............. *A61B 34/37* (2016.02); *A61B 34/74* (2016.02); *A61B 34/76* (2016.02); *A61F 2/40* (2013.01); *A61F 2/4612* (2013.01); *A61B 17/142* (2016.11); *A61B 17/15* (2013.01); *A61B 17/1659* (2013.01); *A61B 17/1684* (2013.01); *A61B 2017/568* (2013.01); *A61B 2034/101* (2016.02); *A61B 2034/104* (2016.02); *A61B 2034/108* (2016.02); *A61B 2034/2051* (2016.02); *A61B 2034/2055* (2016.02); *A61B 2034/743* (2016.02); *A61B 2034/744* (2016.02); *A61B 2090/3945* (2016.02); *A61F 2/30942* (2013.01); *A61F 2002/4632* (2013.01)

(56) References Cited

U.S. PATENT DOCUMENTS

| | | |
|---|---|---|
| RE36,974 E    | 11/2000 | Bonutti |
| 6,205,411 B1  | 3/2001  | DiGioia, III et al. |
| 6,500,195 B2  | 12/2002 | Bonutti |
| 6,702,821 B2  | 3/2004  | Bonutti |
| 6,770,078 B2  | 8/2004  | Bonutti |
| 7,104,996 B2  | 9/2006  | Bonutti |
| 7,206,626 B2  | 4/2007  | Quaid, III |
| 7,206,627 B2  | 4/2007  | Abovitz et al. |
| 7,468,075 B2  | 12/2008 | Lang et al. |
| 7,510,557 B1  | 3/2009  | Bonutti |
| 7,534,263 B2  | 5/2009  | Burdulis, Jr. et al. |
| 7,615,054 B1  | 11/2009 | Bonutti |
| 7,618,451 B2  | 11/2009 | Berez et al. |
| 7,635,390 B1  | 12/2009 | Bonutti |
| 7,708,740 B1  | 5/2010  | Bonutti |
| 7,708,741 B1  | 5/2010  | Bonutti |
| 7,725,162 B2  | 5/2010  | Malackowski et al. |
| 7,747,311 B2  | 6/2010  | Quaid, III |
| 7,749,229 B1  | 7/2010  | Bonutti |
| 7,806,896 B1  | 10/2010 | Bonutti |
| 7,806,897 B1  | 10/2010 | Bonutti |
| 7,828,852 B2  | 11/2010 | Bonutti |
| 7,831,292 B2  | 11/2010 | Quaid et al. |
| 7,837,736 B2  | 11/2010 | Bonutti |
| 7,892,236 B1  | 2/2011  | Bonutti |
| 7,931,690 B1  | 4/2011  | Bonutti |
| 7,959,635 B1  | 6/2011  | Bonutti |
| 7,981,158 B2  | 7/2011  | Fitz et al. |
| 8,010,180 B2  | 8/2011  | Quaid et al. |
| 8,014,984 B2  | 9/2011  | Iannotti et al. |
| 8,066,708 B2  | 11/2011 | Lang et al. |
| 8,083,745 B2  | 12/2011 | Lang et al. |
| 8,095,200 B2  | 1/2012  | Quaid, III |
| 8,105,330 B2  | 1/2012  | Fitz et al. |
| 8,122,582 B2  | 2/2012  | Burdulis, Jr. et al. |
| 8,133,229 B1  | 3/2012  | Bonutti |
| 8,234,097 B2  | 7/2012  | Steines et al. |
| 8,277,454 B2  | 10/2012 | Neubauer et al. |
| 8,287,522 B2  | 10/2012 | Moses et al. |
| 8,337,501 B2  | 12/2012 | Fitz et al. |
| 8,337,507 B2  | 12/2012 | Lang et al. |
| 8,337,508 B2  | 12/2012 | Lavallee et al. |
| 8,343,218 B2  | 1/2013  | Lang et al. |
| 8,361,163 B2  | 1/2013  | Quaid |
| 8,366,771 B2  | 2/2013  | Burdulis, Jr. et al. |
| 8,377,129 B2  | 2/2013  | Fitz et al. |
| 8,380,471 B2  | 2/2013  | Iannotti et al. |
| 8,391,954 B2  | 3/2013  | Quaid, III |
| 8,425,522 B2  | 4/2013  | Bonutti |
| 8,439,926 B2  | 5/2013  | Bojarski et al. |
| 8,439,978 B2  | 5/2013  | Ebbitt |
| 8,457,719 B2  | 6/2013  | Moctezuma de la Barrera et al. |
| 8,460,304 B2  | 6/2013  | Fitz et al. |
| 8,480,754 B2  | 7/2013  | Bojarski et al. |
| 8,498,744 B2  | 7/2013  | Odermatt et al. |
| 8,500,740 B2  | 8/2013  | Bojarski et al. |
| 8,529,630 B2  | 9/2013  | Bojarski et al. |
| 8,551,099 B2  | 10/2013 | Lang et al. |
| 8,551,102 B2  | 10/2013 | Fitz et al. |
| 8,551,103 B2  | 10/2013 | Fitz et al. |
| 8,551,169 B2  | 10/2013 | Fitz et al. |
| 8,556,906 B2  | 10/2013 | Fitz et al. |
| 8,556,907 B2  | 10/2013 | Fitz et al. |
| 8,556,971 B2  | 10/2013 | Lang |
| 8,556,983 B2  | 10/2013 | Bojarski et al. |
| 8,561,278 B2  | 10/2013 | Fitz et al. |
| 8,562,611 B2  | 10/2013 | Fitz et al. |
| 8,562,618 B2  | 10/2013 | Fitz et al. |
| 8,568,479 B2  | 10/2013 | Fitz et al. |
| 8,568,480 B2  | 10/2013 | Fitz et al. |
| 8,585,708 B2  | 11/2013 | Fitz et al. |
| 8,617,172 B2  | 12/2013 | Fitz et al. |
| 8,623,026 B2  | 1/2014  | Wong et al. |
| 8,623,030 B2  | 1/2014  | Bonutti |
| 8,632,552 B2  | 1/2014  | Bonutti |
| 8,641,660 B2  | 2/2014  | Bonutti et al. |
| 8,641,716 B2  | 2/2014  | Fitz et al. |
| 8,641,726 B2  | 2/2014  | Bonutti |
| 8,657,827 B2  | 2/2014  | Fitz et al. |
| 8,690,945 B2  | 4/2014  | Fitz et al. |
| 8,709,016 B2  | 4/2014  | Park et al. |
| 8,731,885 B2  | 5/2014  | Annotti et al. |
| 8,753,346 B2  | 6/2014  | Suarez et al. |
| 8,768,028 B2  | 7/2014  | Lang et al. |
| 8,771,365 B2  | 7/2014  | Bojarski et al. |
| 8,784,495 B2  | 7/2014  | Bonutti |
| 8,801,719 B2  | 8/2014  | Park et al. |
| 8,801,720 B2  | 8/2014  | Park et al. |
| 8,834,490 B2  | 9/2014  | Bonutti |
| 8,840,629 B2  | 9/2014  | Bonutti |
| 8,858,557 B2  | 10/2014 | Bonutti |
| 8,882,779 B2  | 11/2014 | Park et al. |
| 8,906,107 B2  | 12/2014 | Bojarski et al. |
| 8,911,499 B2  | 12/2014 | Quaid et al. |
| 8,926,706 B2  | 1/2015  | Bojarski et al. |
| 8,936,596 B2  | 1/2015  | Mittelstadt et al. |
| 8,951,259 B2  | 2/2015  | Fitz et al. |
| 8,974,539 B2  | 3/2015  | Bojarski et al. |
| 8,977,021 B2  | 3/2015  | Kang et al. |
| 8,979,859 B2  | 3/2015  | Leparmentier et al. |
| 8,992,542 B2  | 3/2015  | Hagag et al. |
| 8,998,915 B2  | 4/2015  | Fitz et al. |
| 9,002,426 B2  | 4/2015  | Quaid et al. |
| 9,008,757 B2  | 4/2015  | Wu |
| 9,020,788 B2  | 4/2015  | Lang et al. |
| 9,023,050 B2  | 5/2015  | Lang et al. |
| 9,055,953 B2  | 6/2015  | Lang et al. |
| 9,060,797 B2  | 6/2015  | Bonutti |
| 9,066,728 B2  | 6/2015  | Burdulis, Jr. et al. |
| 9,072,531 B2  | 7/2015  | Fitz et al. |
| 9,084,617 B2  | 7/2015  | Lang et al. |
| 9,095,353 B2  | 8/2015  | Burdulis, Jr. et al. |
| 9,101,394 B2  | 8/2015  | Arata et al. |
| 9,101,443 B2  | 8/2015  | Bonutti |
| 9,107,679 B2  | 8/2015  | Lang et al. |
| 9,107,680 B2  | 8/2015  | Fitz et al. |
| 9,113,921 B2  | 8/2015  | Lang et al. |
| 9,119,655 B2  | 9/2015  | Bowling et al. |
| 9,125,672 B2  | 9/2015  | Fitz et al. |
| 9,125,673 B2  | 9/2015  | Fitz et al. |

(56) References Cited

U.S. PATENT DOCUMENTS

| | | |
|---|---|---|
| 9,125,753 B2 | 9/2015 | Caballes |
| 9,131,597 B2 | 9/2015 | Taft et al. |
| 9,149,281 B2 | 10/2015 | Bonutti |
| 9,155,544 B2 | 10/2015 | Bonutti |
| 9,186,161 B2 | 11/2015 | Lang et al. |
| 9,192,395 B2 | 11/2015 | Bonutti |
| 9,192,459 B2 | 11/2015 | Bonutti |
| 9,216,025 B2 | 12/2015 | Fitz et al. |
| 9,220,510 B2 | 12/2015 | Cheal et al. |
| 9,220,516 B2 | 12/2015 | Lang et al. |
| 9,220,517 B2 | 12/2015 | Lang et al. |
| 9,226,828 B2 | 1/2016 | Bonutti |
| 9,241,724 B2 | 1/2016 | Lang et al. |
| 9,241,725 B2 | 1/2016 | Lang et al. |
| 9,265,509 B2 | 2/2016 | Park et al. |
| 9,271,766 B2 | 3/2016 | Bonutti |
| 9,275,192 B2 | 3/2016 | Kang et al. |
| 9,289,264 B2 | 3/2016 | Iorgulescu et al. |
| 9,292,657 B2 | 3/2016 | Kang et al. |
| 9,295,481 B2 | 3/2016 | Fitz et al. |
| 9,295,482 B2 | 3/2016 | Fitz et al. |
| 9,308,005 B2 | 4/2016 | Fitz et al. |
| 9,308,053 B2 | 4/2016 | Bojarski et al. |
| 9,314,256 B2 | 4/2016 | Fitz et al. |
| 9,320,620 B2 | 4/2016 | Bojarski et al. |
| 9,326,780 B2 | 5/2016 | Wong et al. |
| 9,358,018 B2 | 6/2016 | Fitz et al. |
| 9,364,291 B2 | 6/2016 | Bellettre et al. |
| 9,375,222 B2 | 6/2016 | Fitz et al. |
| 9,381,025 B2 | 7/2016 | Fitz et al. |
| 9,381,085 B2 | 7/2016 | Axelson, Jr. et al. |
| 9,387,079 B2 | 7/2016 | Bojarski et al. |
| 9,402,726 B2 | 8/2016 | Linderman et al. |
| 9,408,615 B2 | 8/2016 | Fitz et al. |
| 9,439,767 B2 | 9/2016 | Bojarski et al. |
| 9,474,847 B2 | 10/2016 | Bonutti et al. |
| 9,486,227 B2 | 11/2016 | Bonutti |
| 9,492,237 B2 | 11/2016 | Kang et al. |
| 9,495,483 B2 | 11/2016 | Steines et al. |
| 9,545,268 B2 | 1/2017 | Bonutti |
| 9,579,110 B2 | 2/2017 | Bojarski et al. |
| 9,579,129 B2 | 2/2017 | Bonutti |
| 9,585,725 B2 | 3/2017 | Bonutti |
| 9,588,587 B2 | 3/2017 | Otto et al. |
| 9,597,157 B2 | 3/2017 | Hagag et al. |
| 9,603,711 B2 | 3/2017 | Bojarski et al. |
| 9,610,084 B2 | 4/2017 | Walker |
| 9,629,687 B2 | 4/2017 | Bonutti |
| 9,636,185 B2 | 5/2017 | Quaid et al. |
| 9,655,683 B2 | 5/2017 | Iorgulescu et al. |
| 9,665,686 B2 | 5/2017 | Vorhis et al. |
| 9,687,308 B2 | 6/2017 | Windolf et al. |
| 2003/0055502 A1 | 3/2003 | Lang et al. |
| 2006/0089646 A1 | 4/2006 | Bonutti |
| 2006/0142657 A1 | 6/2006 | Quaid et al. |
| 2007/0066917 A1 | 3/2007 | Hodorek et al. |
| 2007/0179626 A1 | 8/2007 | Barrera et al. |
| 2007/0282450 A1 | 12/2007 | Habermeyer et al. |
| 2008/0004633 A1 | 1/2008 | Arata et al. |
| 2008/0010705 A1 | 1/2008 | Quaid et al. |
| 2008/0058945 A1 | 3/2008 | Hajaj et al. |
| 2009/0000626 A1 | 1/2009 | Quaid et al. |
| 2009/0012532 A1 | 1/2009 | Quaid et al. |
| 2009/0157192 A1 | 6/2009 | Stuart |
| 2010/0106194 A1 | 4/2010 | Bonutti et al. |
| 2010/0153081 A1 | 6/2010 | Bellettre et al. |
| 2010/0217400 A1 | 8/2010 | Nortman et al. |
| 2010/0329530 A1 | 12/2010 | Lang et al. |
| 2011/0060375 A1 | 3/2011 | Bonutti |
| 2011/0071528 A1 | 3/2011 | Carson |
| 2011/0071529 A1 | 3/2011 | Carson |
| 2011/0071530 A1 | 3/2011 | Carson |
| 2011/0071531 A1 | 3/2011 | Carson |
| 2011/0071532 A1 | 3/2011 | Carson |
| 2011/0071645 A1 | 3/2011 | Bojarski et al. |
| 2011/0082587 A1 | 4/2011 | Ziaei et al. |
| 2011/0213374 A1 | 9/2011 | Fitz et al. |
| 2011/0213377 A1 | 9/2011 | Lang et al. |
| 2011/0213428 A1 | 9/2011 | Fitz et al. |
| 2011/0213429 A1 | 9/2011 | Lang et al. |
| 2011/0238073 A1 | 9/2011 | Lang et al. |
| 2011/0313423 A1 | 12/2011 | Lang et al. |
| 2012/0010623 A1 | 1/2012 | Bonutti |
| 2012/0066892 A1 | 3/2012 | Lang et al. |
| 2012/0071883 A1 | 3/2012 | Lang et al. |
| 2012/0109150 A1 | 5/2012 | Quaid et al. |
| 2012/0109152 A1 | 5/2012 | Quaid, III |
| 2012/0191205 A1 | 7/2012 | Bojarski et al. |
| 2012/0191420 A1 | 7/2012 | Bojarski et al. |
| 2012/0197408 A1 | 8/2012 | Lang et al. |
| 2012/0215226 A1 | 8/2012 | Bonutti |
| 2012/0226198 A1 | 9/2012 | Carson |
| 2012/0226481 A1 | 9/2012 | Carson |
| 2012/0245699 A1 | 9/2012 | Lang et al. |
| 2012/0310617 A1 | 12/2012 | Bellettre et al. |
| 2013/0103363 A1 | 4/2013 | Lang et al. |
| 2013/0110471 A1 | 5/2013 | Lang et al. |
| 2013/0211531 A1 | 8/2013 | Steines et al. |
| 2013/0226185 A1 | 8/2013 | Bonutti |
| 2013/0237989 A1 | 9/2013 | Bonutti |
| 2013/0238039 A1 | 9/2013 | Bonutti |
| 2013/0245803 A1 | 9/2013 | Lang |
| 2013/0289729 A1 | 10/2013 | Bonutti |
| 2014/0005792 A1 | 1/2014 | Lang et al. |
| 2014/0031826 A1 | 1/2014 | Bojarski et al. |
| 2014/0066959 A1 | 3/2014 | Bonutti |
| 2014/0142710 A1 | 5/2014 | Lang |
| 2014/0188134 A1 | 7/2014 | Nortman et al. |
| 2014/0188240 A1 | 7/2014 | Lang et al. |
| 2014/0194989 A1 | 7/2014 | Bonutti |
| 2014/0200621 A1 | 7/2014 | Malackowski et al. |
| 2014/0228860 A1 | 8/2014 | Steines et al. |
| 2014/0309560 A1 | 10/2014 | Bonutti |
| 2014/0330278 A1 | 11/2014 | Park et al. |
| 2014/0330279 A1 | 11/2014 | Park et al. |
| 2015/0032217 A1 | 1/2015 | Bojarski et al. |
| 2015/0185846 A1* | 7/2015 | Otto .................. G06F 3/016 345/156 |
| 2015/0250597 A1 | 9/2015 | Lang et al. |
| 2015/0257768 A1 | 9/2015 | Bonutti |
| 2015/0320500 A1 | 11/2015 | Lightcap et al. |
| 2015/0335444 A1 | 11/2015 | Caballes |
| 2016/0015466 A1 | 1/2016 | Park et al. |
| 2016/0030126 A1 | 2/2016 | Netravali et al. |
| 2016/0038243 A1 | 2/2016 | Miller et al. |
| 2016/0038244 A1 | 2/2016 | Netravali et al. |
| 2016/0038291 A1 | 2/2016 | Netravali et al. |
| 2016/0074124 A1 | 3/2016 | Fitz et al. |
| 2016/0081758 A1 | 3/2016 | Bonutti |
| 2016/0095609 A1 | 4/2016 | Park et al. |
| 2016/0143744 A1 | 5/2016 | Bojarski et al. |
| 2016/0143749 A1 | 5/2016 | Holovacs et al. |
| 2016/0175054 A1 | 6/2016 | Kang et al. |
| 2016/0199136 A1 | 7/2016 | Iorgulescu et al. |
| 2016/0206331 A1 | 7/2016 | Fitz et al. |
| 2016/0206375 A1 | 7/2016 | Abbasi et al. |
| 2016/0206377 A1 | 7/2016 | Cheal et al. |
| 2016/0228193 A1 | 8/2016 | Moctezuma de la Barrera et al. |
| 2016/0228204 A1 | 8/2016 | Quaid et al. |
| 2016/0242931 A1 | 8/2016 | Wong et al. |
| 2016/0262910 A1 | 9/2016 | Axelson, Jr. et al. |
| 2016/0310282 A1 | 10/2016 | Bojarski et al. |
| 2016/0317312 A1 | 11/2016 | Bojarski et al. |
| 2016/0324581 A1 | 11/2016 | Bojarski et al. |
| 2016/0331467 A1 | 11/2016 | Slamin et al. |
| 2016/0331481 A1 | 11/2016 | Bonutti |
| 2016/0374693 A1 | 12/2016 | Van Citters et al. |
| 2017/0000562 A1 | 1/2017 | Frank et al. |
| 2017/0007275 A1 | 1/2017 | Park et al. |
| 2017/0007331 A1 | 1/2017 | Couture et al. |
| 2017/0007408 A1 | 1/2017 | Fitz et al. |
| 2017/0020613 A1 | 1/2017 | Kang et al. |
| 2017/0049487 A1 | 2/2017 | Bonutti et al. |
| 2017/0056022 A1 | 3/2017 | Cheal et al. |

(56) References Cited

U.S. PATENT DOCUMENTS

| | | |
|---|---|---|
| 2017/0056183 A1 | 3/2017 | Steines et al. |
| 2017/0065347 A1 | 3/2017 | Bojarski et al. |
| 2017/0079803 A1 | 3/2017 | Lang |
| 2017/0119531 A1 | 5/2017 | Bojarski et al. |
| 2017/0151021 A1 | 6/2017 | Quaid, III |
| 2017/0164957 A1 | 6/2017 | Bojarski et al. |
| 2017/0172665 A1 | 6/2017 | Otto et al. |
| 2017/0181755 A1 | 6/2017 | Librot |
| 2017/0181798 A1 | 6/2017 | Panescu et al. |
| 2017/0189203 A1 | 7/2017 | Hagag et al. |
| 2018/0271667 A1 | 9/2018 | Kemp et al. |

FOREIGN PATENT DOCUMENTS

| | | |
|---|---|---|
| WO | 2010068212 A1 | 6/2010 |
| WO | 2010068213 A1 | 6/2010 |
| WO | 2016094298 A1 | 6/2016 |
| WO | 2016115306 A1 | 7/2016 |
| WO | 2016115423 A1 | 7/2016 |

OTHER PUBLICATIONS

Arthrex, Inc., "Patient's Guide to Shoulder Replacement Surgery with the Arthrex Eclipse and Univers II Brochure", 2015, 12 pages.
Biomet Orthopedics, "Comprehensive Nano Stemless Shoulder Anatomic and Reverse Brochure", 2012, 60 pages.
Biomet Orthopedics, "T.E.S.S. Shoulder System Surgical Technique Brochure", 2011, 43 pages.
Casagrande Md, Danielle J. et al., "Radiographic Evaluation of Short-Stem Press-Fit Total Shoulder Arthroplasty: Short-Term Follow-Up", Journal of Shoulder and Elbow Surgery, vol. 25, Issue 7, Jul. 2016, pp. 1163-1169.
Choi et al., "Visbone: 3D Visualization of Bone Mineral Density", Pacific Conference on Computer Graphics and Applications, IEEE Computer Society, 1999, pp. 138-146.
Costouros, Md Facs, John G., "Stemless Shoulder Arthroplasty Presentation", 2017, 41 pages.
FX Solutions, "Easytech Anatomical Surgical Technique Brochure", 2016, 8 pages.
Harmer, L. et al., "Total Shoulder Arthroplasty: Are the Humeral Components Getting Shorter?", Curr. Rev. Muscuskelet. Med., vol. 9, Issue 1, Mar. 2016, pp. 17-22.
Lima Corporate, "SMR System Surgical Technique Brochure", 2015, 62 pages.
Mathys European Orthopaedics, Affinis Short—Short Stemmed Total Shoulder Prosthesis Brochure, 2016, 28 pages.
Nguyen, Duong et al., "Improved Accuracy of Computer-Assisted Glenoid Implantation in Total Shoulder Arthroplasty: An In-Vitro Randomized Controlled Trial", Journal of Shoulder and Elbow Surgery, vol. 18, 2009, pp. 907-914.
Pandey, Rupesh Kumar et al., "Drilling of Bone: A Comprehensive Review", Journal of Orthopaedics and Trauma, vol. 4, 2013, pp. 15-30.
Schnetzke, M. et al., "Radiologic Bone Adaptations on a Cementless Short-Stem Shoulder Prosthesis", J. Shoulder Elbow Surg., vol. 25, Issue 4, Apr. 2016, pp. 650-657.
Stryker, "Reunion TSA—Total Shoulder Arthroplasty System-Operative Technique", Sep. 2016, pp. 1-88.
Wright, "Tornier Simpliciti Shoulder System Surgical Technique Brochure", 2016, 24 pages.
Zimmer Biomet, "Sidus Stem-Free Shoulder Brochure", Jan. 2018, 40 pages.
Atmani, H. et al., "Computer-Aided Surgery System for Shoulder Prosthesis Placement", Computer Aided Surgery, vol. 12, No. 1, Jan. 2007, pp. 60-70.

* cited by examiner

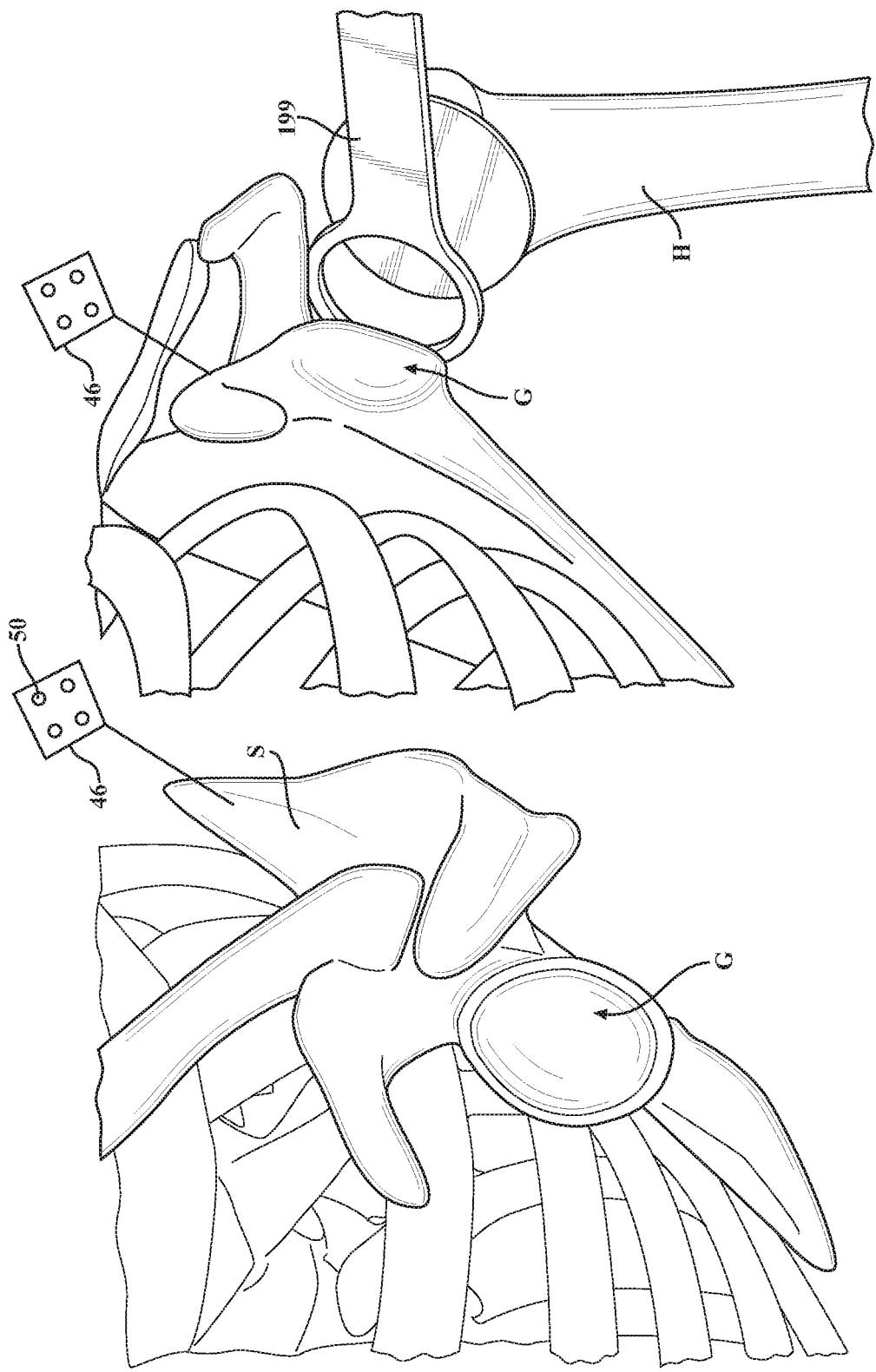

ROBOTIC SYSTEM FOR SHOULDER ARTHROPLASTY USING STEMLESS IMPLANT COMPONENTS

RELATED APPLICATIONS

This application claims priority to and the benefit of U.S. Provisional Patent Application No. 62/582,620, filed on Nov. 7, 2017, the disclosure of which is hereby incorporated herein by reference.

TECHNICAL FIELD

The present disclosure relates generally to robotic systems and, more particularly, to robotic systems for shoulder arthroplasty.

BACKGROUND

Robotic systems used in surgery are well known. One such system comprises a robotic manipulator and a cutting tool for sculpting a bone into a desired shape. The cutting tool is coupled to the robotic manipulator to remove material from the bone for purposes of creating space to receive an implant. Typically, these systems are used to prepare bones for hip implants and knee implants. As the world population continues to live longer, there is a growing need for arthroplasty. Owing to the relatively greater need for hip arthroplasty and knee arthroplasty, prior art robotic systems focus on preparing bones for hip and knee procedures. There remains a need for robotic systems for shoulder arthroplasty to provide higher accuracy and more precision in replacing shoulder joints.

Shoulder arthroplasty procedures commonly involve preparing a patient's humerus to receive a stemmed implant and preparing the patient's glenoid cavity to receive a glenoid implant. However, in some cases, instead of preparing the humerus to receive a stemmed implant, the humerus is prepared for a stemless implant. Generally speaking, stemless implants are bone-sparing, meaning that less bony material is required to be removed from the patient as compared to stemmed implants. This can provide several advantages to the patient. Yet, because a stem is not placed in the humerus, i.e., in a humeral canal that can enhance stability of the implant, there is a desire and need for stemless implants and procedures that securely place such stemless implants in the humerus.

SUMMARY

A robotic surgery system is provided for preparing a humerus to receive a shoulder implant. The robotic surgery system comprises a robotic manipulator and a cutting tool to be coupled to the robotic manipulator. A localizer is configured to track movement of the cutting tool and the humerus. A controller is coupled to the robotic manipulator and the localizer. The controller is configured to operate the robotic manipulator to control movement of the cutting tool relative to the humerus based on a virtual object that defines a volume of material to be removed from the humerus to receive the shoulder implant. The controller is further configured to determine positions of a plurality of landmarks on the humerus, define a virtual resection in a coordinate system based on the plurality of landmarks, and define the virtual object in the coordinate system based on a location of the virtual resection.

A method is provided for performing robotic surgery with a robotic manipulator and a cutting tool coupled to the robotic manipulator to prepare a humerus to receive a shoulder implant. The method comprises determining positions of a plurality of landmarks on the humerus and defining a virtual resection in a coordinate system based on the positions of the plurality of landmarks. A virtual object is defined in the coordinate system based on a location of the virtual resection wherein the virtual object defines a volume of material to be removed from the humerus to receive the shoulder implant. The method further comprises tracking movement of the cutting tool, tracking movement of the humerus, and controlling movement of the cutting tool relative to the humerus based on the virtual object to remove the volume of material from the humerus.

Another robotic surgery system is provided for preparing a humerus to receive a stemless shoulder implant. The robotic surgery system comprising a robotic manipulator and a cutting tool to be coupled to the robotic manipulator. A localizer is configured to track movement of the cutting tool and the humerus. A controller is coupled to the robotic manipulator and the localizer. The controller is configured to operate the robotic manipulator to control movement of the cutting tool relative to the humerus based on a virtual object that defines a volume of material to be removed from the humerus to receive the stemless shoulder implant. The controller is further configured to: define a virtual intramedullary axis of the humerus in a coordinate system prior to resecting a humeral head of the humerus; determine positions of a plurality of landmarks on the humerus; plan a resection of the humeral head based on a location of the virtual intramedullary axis and the positions of the plurality of landmarks; and define the virtual object in the coordinate system based on the planned resection.

Another method is provided for performing robotic surgery with a robotic manipulator and a cutting tool coupled to the robotic manipulator to prepare a humerus to receive a shoulder implant. The method comprises defining a virtual intramedullary axis of the humerus in a coordinate system prior to resecting a humeral head of the humerus and determining positions of a plurality of landmarks on the humerus. A resection of the humeral head is planned based on a location of the virtual intramedullary axis and the positions of the plurality of landmarks. A virtual object is defined in the coordinate system based on the planned resection, wherein the virtual object defines a volume of material to be removed from the humerus to receive the shoulder implant. The method further comprises tracking movement of the cutting tool, tracking movement of the humerus, and controlling movement of the cutting tool relative to the humerus based on the virtual object to remove the volume of material from the humerus.

Another method is provided for planning a surgery to prepare a humerus to receive a stemless shoulder implant based on a future location of a stemmed shoulder implant to be placed in the humerus during a revision surgery. The method comprises defining the future location of the stemmed shoulder implant in a coordinate system associated with the humerus, wherein the future location is defined in the coordinate system prior to resecting a humeral head of the humerus and prior to removing a volume of material from the humerus to receive the stemless shoulder implant. The method also comprises planning a location of the stemless shoulder implant in the coordinate system based on the future location of the stemmed shoulder implant defined in the coordinate system so that movement of one or more cutting tools can be controlled to resect the humeral head and remove the volume of material from the humerus to receive the stemless shoulder implant based on the planned location of the stemless shoulder implant, which is derived from the future location of the stemmed shoulder implant.

BRIEF DESCRIPTION OF THE DRAWINGS

Advantages of the present disclosure will be readily appreciated as the same becomes better understood by reference to the following detailed description when considered in connection with the accompanying drawings.

FIGS. 9-14 illustrate various steps taken to prepare a glenoid cavity of the shoulder joint to receive a glenoid component of the shoulder implant system.

DETAILED DESCRIPTION

Figure 1:
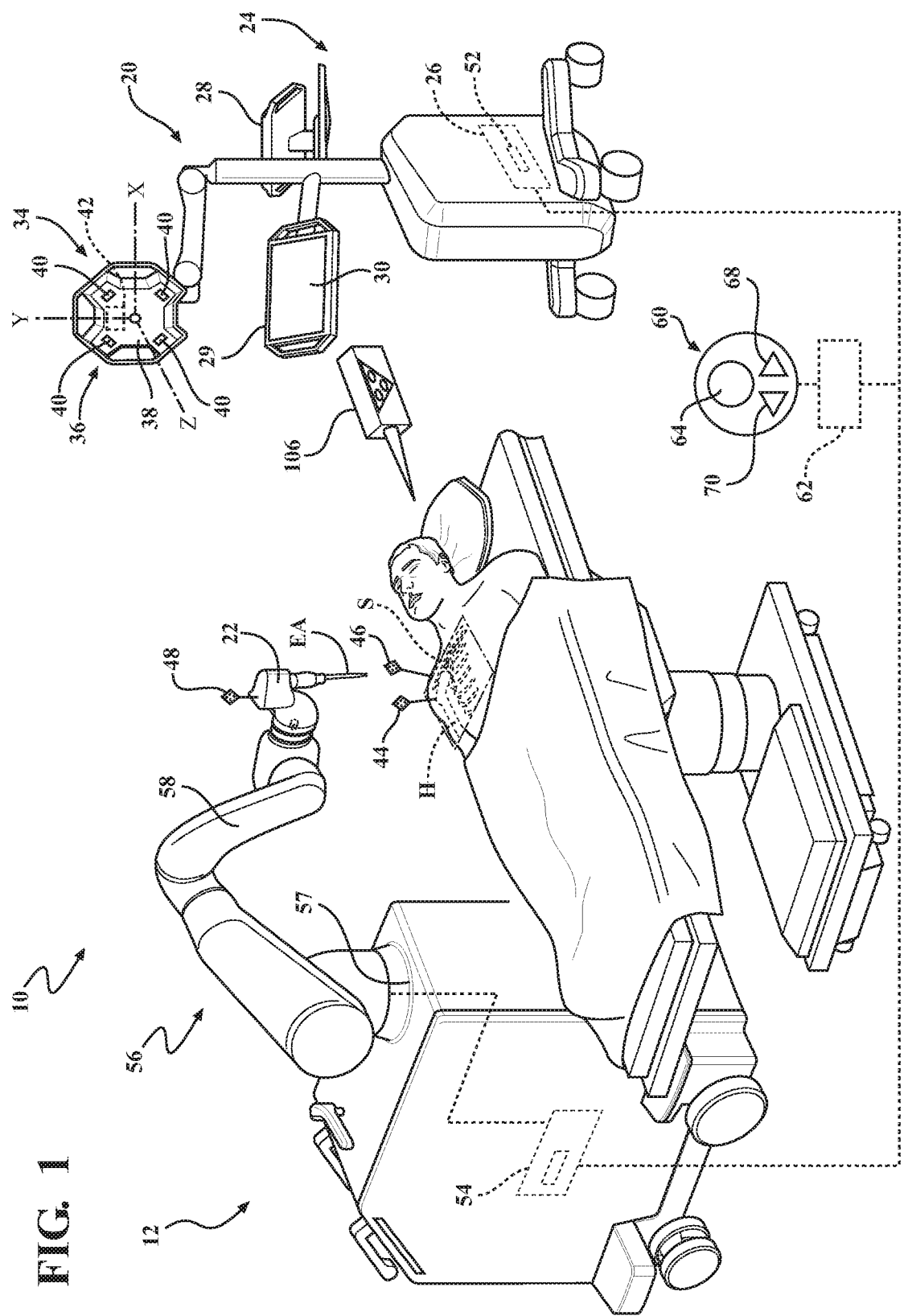
FIG. 1 is a perspective view of a robotic system for shoulder arthroplasty.

Referring to FIG. 1, a robotic system 10 is illustrated for performing surgery on a patient. The version shown in FIG. 1 comprises a material removal system for removing material from a workpiece (e.g., bone), but it should be appreciated that other types of robotic systems are also contemplated. The robotic system 10 is shown in a surgical setting such as an operating room of a medical facility. In the embodiment shown, the robotic system 10 includes a machining station 12 and a guidance station 20.

The guidance station 20 is set up to track movement of various objects in the operating room. Such objects include, for example, a surgical tool 22, a humerus H of a patient, and a scapula S of the patient. The guidance station 20 tracks these objects for purposes of displaying their relative positions and orientations to the surgeon and, in some cases, for purposes of controlling movement (e.g., causing movement, guiding movement, constraining movement, etc.) of the surgical tool 22 relative to virtual cutting boundaries or other virtual objects associated with the humerus H and scapula S.

The guidance station 20 includes a computer cart assembly 24 that houses a navigation controller 26. A navigation interface is in operative communication with the navigation controller 26. The navigation interface includes a first display 28 adapted to be situated outside of a sterile field and a second display 29 adapted to be situated inside the sterile field. The displays 28, 29 are adjustably mounted to the computer cart assembly 24. First and second input devices such as a keyboard and mouse can be used to input information into the navigation controller 26 or otherwise select/control certain aspects of the navigation controller 26. Other input devices are contemplated including a touch screen 30 or voice-activation.

A localizer 34 communicates with the navigation controller 26. In the embodiment shown, the localizer 34 is an optical localizer and includes a camera unit 36. Other types of localizers are also contemplated, including localizers that employ ultrasound, radio frequency (RF) signals, electromagnetic fields, and the like. The camera unit 36 has an outer casing 38 that houses one or more optical position sensors 40. In some embodiments at least two optical sensors 40 are employed, preferably three or four. The optical sensors 40 may be four separate charge-coupled devices (CCD). In one embodiment four, one-dimensional CCDs are employed. It should be appreciated that in other embodiments, separate camera units, each with a separate CCD, or two or more CCDs, could also be arranged around the operating room. The CCDs detect infrared (IR) signals.

The camera unit 36 is mounted on an adjustable arm to position the optical sensors 40 with a field of view of the below discussed trackers that, ideally, is free from obstructions. In some embodiments the camera unit 36 is adjustable in at least one degree of freedom by rotating about a rotational joint. In other embodiments, the camera unit 36 is adjustable about two or more degrees of freedom.

The camera unit 36 includes a camera controller 42 in communication with the optical sensors 40 to receive signals from the optical sensors 40. The camera controller 42 communicates with the navigation controller 26 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors 40 communicate directly with the navigation controller 26.

Position and orientation signals and/or data are transmitted to the navigation controller 26 for purposes of tracking objects. The computer cart assembly 24, display 28, and camera unit 36 may be like those described in U.S. Pat. No. 7,725,162 to Malackowski, et al. issued on May 25, 2010, entitled "Surgery System," hereby incorporated by reference.

The navigation controller 26 can be a personal computer or laptop computer. The navigation controller 26 has the display 28, central processing unit (CPU) and/or other processors, memory (not shown), and storage (not shown). The navigation controller 26 is loaded with software. The software converts the signals received from the camera unit 36 into data representative of the position and orientation of the objects being tracked.

The guidance station 20 is operable with a plurality of tracking devices 44, 46, 48, also referred to herein as trackers. In the illustrated embodiment, one tracker 44 is firmly affixed to the humerus H of the patient and another tracker 46 is firmly affixed to the scapula S of the patient. The trackers 44, 46 are firmly affixed to sections of bone. The trackers 44, 46 could be mounted like those shown in U.S. Patent Application Publication No. 2014/0200621, published on Jul. 17, 2014, entitled, "Navigation Systems and Methods for Indicating and Reducing Line-of-Sight Errors," the entire disclosure of which is hereby incorporated by reference. The trackers 44, 46 could be mounted to other tissue types or parts of the anatomy.

A tool tracker 48 is firmly attached to the surgical tool 22. The tool tracker 48 may be integrated into the surgical tool 22 during manufacture or may be separately mounted to the surgical tool 22 in preparation for surgical procedures. In the embodiment shown, the surgical tool 22 is attached to a manipulator 56 of the machining station 12. Such an arrangement is shown in U.S. Pat. No. 9,119,655, issued Sep. 1, 2015, entitled, "Surgical Manipulator Capable of Controlling a Surgical Instrument in Multiple Modes," the entire disclosure of which is hereby incorporated by reference.

A separate tracker (not shown) may be attached to a base 57 of the manipulator 56 to track movement of the base 57 in some embodiments. In this case, the working end of the surgical tool 22 may be tracked via the base tracker by virtue of additional encoder data being provided by encoders in joints of the manipulator 56, which provide joint position data that can be collectively processed to generate information regarding a location of the working end of the surgical tool 22 relative to the base 57. The working end of the surgical tool 22, which is being tracked by virtue of the tool tracker 48 (or base tracker in some cases), may be an energy applicator EA such as a rotating bur, saw blade, electrical ablation device, or the like. The energy applicator EA may be a separate component that is releasably connected to a handpiece of the surgical tool 22 or may be integrally formed with the handpiece.

The trackers 44, 46, 48 can be battery powered with an internal battery or may have leads to receive power through the navigation controller 26, which, like the camera unit 36, receives external power.

The optical sensors 40 of the localizer 34 receive light signals from the trackers 44, 46, 48. In the illustrated embodiment, the trackers 44, 46, 48 are active trackers. In this embodiment, each tracker 44, 46, 48 has at least three active tracking elements or markers for transmitting light signals to the optical sensors 40. The active markers can be, for example, light emitting diodes or LEDs 50 (see FIG. 2) transmitting light, such as infrared light. The optical sensors 40 preferably have sampling rates of 100 Hz or more, more preferably 300 Hz or more, and most preferably 500 Hz or more. In some embodiments, the optical sensors 40 have sampling rates of 8000 Hz. The sampling rate is the rate at which the optical sensors 40 receive light signals from sequentially fired LEDs (not shown). In some embodiments, the light signals from the LEDs 50 are fired at different rates for each tracker 44, 46, 48.

Each of the LEDs 50 are connected to a tracker controller (not shown) located in a housing of the associated tracker 44, 46, 48 that transmits/receives data to/from the navigation controller 26. In one embodiment, the tracker controllers transmit data on the order of several Megabytes/second through wired connections with the navigation controller 26. In other embodiments, a wireless connection may be used. In these embodiments, the navigation controller 26 has a transceiver (not shown) to receive the data from the tracker controller.

In other embodiments, the trackers 44, 46, 48 may have passive markers (not shown), such as reflectors that reflect light emitted from the camera unit 36. The reflected light is then received by the optical sensors 40. Active and passive arrangements are well known in the art.

In some embodiments, the trackers 44, 46, 48 also include a gyroscope sensor and accelerometer, such as the trackers shown in U.S. Pat. No. 9,008,757, issued on Apr. 14, 2015, entitled, "Navigation System Including Optical and Non-Optical Sensors," the entire disclosure of which is hereby incorporated by reference.

The navigation controller 26 includes a navigation processor 52. It should be understood that the navigation processor 52 could include one or more processors to control operation of the navigation controller 26. The processors can be any type of microprocessor or multi-processor system.

The navigation controller 26 may additionally or alternatively comprise one or more microcontrollers, field programmable gate arrays, systems on a chip, discrete circuitry, and/or other suitable hardware, software, or firmware that is capable of carrying out the functions described herein. The term processor is not intended to limit the scope of any embodiment to a single processor.

The camera unit 36 receives optical signals from the LEDs 50 of the trackers 44, 46, 48 and outputs to the processor 52 signals relating to the position of the LEDs 50 of the trackers 44, 46, 48 relative to the localizer 34. Based on the received optical (and non-optical signals in some embodiments), navigation processor 52 generates data indicating the relative positions and orientations of the trackers 44, 46, 48 relative to the localizer 34 using triangulation and/or other techniques.

Prior to the start of the surgical procedure, additional data are loaded into the navigation processor 52. Based on the position and orientation of the trackers 44, 46, 48 and the previously loaded data, the navigation processor 52 determines the position of the working end of the surgical tool 22 (e.g., the centroid of a surgical bur, cutting envelope of a sagittal saw, etc.) and the orientation of the surgical tool 22 relative to the tissue against which the working end is to be applied. In some embodiments, the navigation processor 52 forwards these data to a manipulator controller 54. The manipulator controller 54 can then use the data to control the manipulator 56 as described in U.S. Pat. No. 9,119,655, issued Sep. 1, 2015, entitled, "Surgical Manipulator Capable of Controlling a Surgical Instrument in Multiple Modes," the entire disclosure of which is hereby incorporated by reference.

In one embodiment, the surgical tool 22 is controlled to stay within one or more preoperatively defined virtual boundaries set by the surgeon, which defines the material (e.g., tissue) of the humerus H and scapula S to be removed by the surgical tool 22. These boundaries are defined by virtual objects stored in memory in the robotic system 10 (e.g., in the navigation controller 26 and/or the manipulator controller 54). The boundaries may be defined within a virtual model of the humerus H and scapula S and be represented as a mesh surface, constructive solid geometry (CSG), voxels, or may be represented using other boundary representation techniques. The boundaries may also be defined separately from virtual models of the humerus H and scapula S.

The navigation processor 52 also generates image signals that indicate the relative position of the working end of the surgical tool 22 to the tissue to be removed. These image signals are applied to the displays 28, 29. The displays 28, 29, based on these signals, generate images that allow the surgeon and staff to view the relative position of the working end to the surgical site. The displays, 28, 29, as discussed above, may include a touch screen or other input/output device that allows entry of commands.

In the embodiment shown in FIG. 1, the surgical tool 22 forms part of an end effector of the manipulator 56. The manipulator 56 has a plurality of links 58 extending from the base 57, and a plurality of active joints (not numbered) for moving the surgical tool 22 with respect to the base 57. The links 58 may form a serial robotic arm structure as shown, a parallel robotic arm structure (not shown), or other suitable structure.

The manipulator 56 has the ability to operate in one or more of: (1) a free mode in which a user grasps the end effector of the manipulator 56 in order to cause movement of the surgical tool 22 (e.g., directly, through force/torque sensor measurements that cause active driving of the manipulator 56, passively, or otherwise); (2) a haptic mode in which the user grasps the end effector of the manipulator 56 to cause movement as in the free mode, but is restricted in movement by the virtual boundaries defined by the virtual objects stored in the robotic system 10; (3) a semi-autonomous mode in which the surgical tool 22 is moved by the manipulator 56 along a tool path (e.g., the active joints of the manipulator 56 are operated to move the surgical tool 22 without requiring force/torque on the end effector from the user); (4) a service mode in which the manipulator 56 performs preprogrammed automated movements to enable servicing; or (5) other modes to facilitate preparation of the manipulator 56 for use, e.g., for draping, etc. Examples of operation in the haptic mode and the semi-autonomous mode are described in U.S. Pat. No. 8,010,180, issued Aug. 30, 2011, entitled, "Haptic Guidance System and Method" and U.S. Pat. No. 9,119,655, issued Sep. 1, 2015, entitled, "Surgical Manipulator Capable of Controlling a Surgical Instrument in Multiple Modes," the entire disclosures of both of which are hereby incorporated by reference.

During operation in the haptic mode, for certain surgical tasks, the user manually manipulates (e.g., manually moves or manually causes the movement of) the manipulator 56 to manipulate the surgical tool 22 to perform the surgical procedure on the patient, such as drilling, cutting, reaming, implant installation, and the like. As the user manipulates the surgical tool 22, the guidance station 20 tracks the location of the surgical tool 22 and/or the manipulator 56 and provides haptic feedback (e.g., force feedback) to the user to limit the user's ability to manually move (or manually cause movement of) the surgical tool 22 beyond one or more predefined virtual boundaries that are registered (mapped) to the patient's anatomy, which results in highly accurate and repeatable drilling, cutting, reaming, and/or implant placement.

The manipulator controller 54 may have a central processing unit (CPU) and/or other manipulator processors, memory (not shown), and storage (not shown). The manipulator controller 54 is loaded with software as described below. The manipulator processors could include one or more processors to control operation of the manipulator 56. The processors can be any type of microprocessor, multi-processor, and/or multi-core processing system. The manipulator controller 54 may additionally or alternatively comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor.

In one version, in the haptic mode, the manipulator controller 54 determines the desired location to which the surgical tool 22 should be moved based on forces and torques applied by the user on the surgical tool 22. In this version, most users are physically unable to actually move the manipulator 56 any appreciable amount to reach the desired position, but the manipulator 56 emulates the user's desired positioning by sensing the applied forces and torques and reacting in a way that gives the user the impression that the user is actually moving the surgical tool 22 even though active motors on the joints are performing the movement. For example, based on the determination of the desired location to which the user wishes to move, and information relating to the current location (e.g., pose) of the surgical tool 22, the manipulator controller 54 determines the extent to which each of the plurality of links 58 needs to be moved in order to reposition the surgical tool 22 from the current location to the desired location. The data regarding where the plurality of links 58 are to be positioned is forwarded to joint motor controllers (not shown) (e.g., one for controlling each motor) that control the active joints of the manipulator 56 to move the plurality of links 58 and thereby move the surgical tool 22 from the current location to the desired location.

A user control pendant assembly 60 may be used to interface with the manipulator controller 54 in the semi-autonomous mode and/or to switch between the free mode, haptic mode, semi-autonomous mode, service mode, and/or other modes. The user control pendant assembly 60 includes a processor or pendant controller 62. The pendant controller 62 may have a central processing unit (CPU) and/or other pendant processors, memory (not shown), and storage (not shown). The pendant controller 62 is in communication with the manipulator controller 54. The pendant controller 62 is also in communication with switches (not shown) associated with user controls such as buttons 64, 68, 70. The pendant processor could include one or more processors to transmit signals resulting from pressing of buttons 64, 68, 70 on the user control pendant assembly 60 to the manipulator controller 54. Once the practitioner is ready to begin autonomous advancement of the surgical tool 22, in the semi-autonomous mode, for example, the practitioner depresses button 64 (and may be required to hold down button 64 to continue autonomous operation). In some versions, based on the depression of buttons 68 and 70, a feed rate (e.g., velocity) of the working end of the surgical tool 22 may be controlled.

Figure 3:
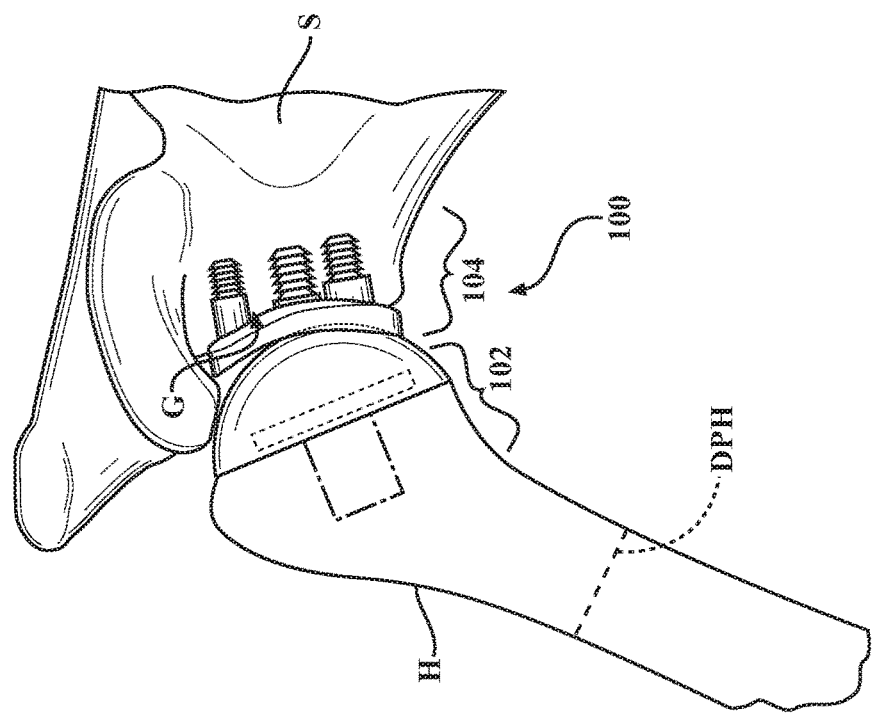
FIG. 3 is an illustration of a shoulder implant system replacing the natural shoulder joint.
Figure 2:
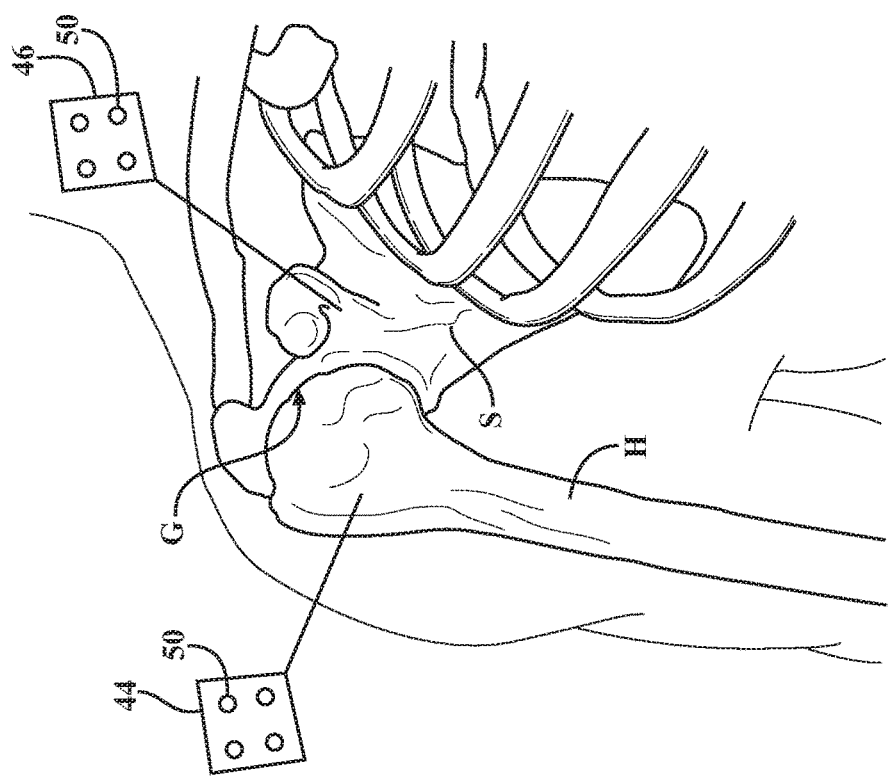
FIG. 2 is an illustration of a shoulder joint requiring arthroplasty.

Referring to FIGS. 2 and 3, pre-operative imaging and/or intra-operative imaging may be employed to visualize the patient's anatomy that requires treatment—such as the patient's shoulder joint. The surgeon plans where to place a shoulder implant system 100 with respect to the images and/or with respect to one or more 3-D models created from the images, such as 3-D models of the humerus H and the scapula S created from CT scan data, MRI data, or the like. Such models may also be based on generic bone models morphed to resemble patient specific anatomy. Planning includes determining a pose of each implant component of the shoulder implant system 100 with respect to the particular bone in which they are being placed, e.g., by identifying the desired pose of the implant component in the images and/or the appropriate 3-D model. This may include creating or positioning a separate 3-D model of the implant components with respect to the 3-D models of the patient's anatomy. Once the plan is set, then the plan is transferred to the robotic system 10 for execution. The 3-D models may comprise mesh surfaces, constructive solid geometries (CSG), voxels, or may be represented using other 3-D modeling techniques.

The robotic system 10 may be employed to prepare the humerus H and a glenoid cavity G of a scapula S to receive the shoulder implant system 100. In this case, the shoulder implant system 100 comprises a humeral component 102 and a glenoid component 104. The humerus H is prepared by the robotic system 10 to receive the humeral component 102, which in some embodiments is stemless and the glenoid cavity G is prepared by the robotic system 10 to receive the glenoid component 104.

Virtual boundaries, pre-defined tool paths, and/or other autonomous movement instructions, that correspond to the desired placement of the humeral component 102 and the glenoid component 104 are created to control movement of the manipulator 56 so that the working end of the surgical tool 22 (e.g., bur, drill, saw) are controlled in a manner that ultimately places the components 102, 104 according to the user's plan. This may comprise ensuring during the surgical procedure that the surgical tool 22 (or cutting accessory attached to it) stays within a pre-defined cutting volume delineating the bounds of the material to be removed to receive the implant. This may also comprise, for example, ensuring during the surgical procedure that a trajectory of the surgical tool 22 is aligned with a desired pose of peg holes, that the trajectory of the surgical tool 22 is aligned with a desired pose of pilot holes for anchoring screws, and the like. This may further comprise ensuring that a plane of the surgical tool 22 (e.g., for a sagittal saw) is aligned with a desired pose of a planar resection.

The robotic system 10 and/or the user may pre-operatively plan the desired cutting volume, trajectories, planar cuts, etc. For example, the desired cutting volumes may simply correspond to the geometry of the implants being used. Furthermore, these cutting volumes may be virtually located and registered to the anatomy by virtue of the user planning the location of the implants relative to the 3-D models of the humerus H and scapula S and registering the 3-D models of the implants, along with the 3-D models of the humerus H and the scapula S to the actual humerus H and scapula S during the procedure.

The robotic system 10 and/or the user may also intra-operatively plan the desired cutting volume, trajectories, planar cuts, etc. or may intra-operatively adjust the cutting volumes, trajectories, planar cuts, etc. that were defined pre-operatively. For example, in the free mode, the user could position a drill or bur at a desired entry point relative to the anatomy of interest, e.g., the humerus, and orient the drill or bur until the display 28, 29 shows that the trajectory of a rotational axis of the drill or bur is in a desired orientation. Once the user is satisfied with the trajectory, the user provides input to the robotic system 10 to set this trajectory as the desired trajectory to be maintained during the procedure. The input could be provided via input devices such as the mouse, keyboard, touchscreen, push button, foot pedal, etc. coupled to the navigation controller 26 or the manipulator controller 54. This same procedure can be followed for the user to set a desired planar cut, etc. 3-D models of the cutting volumes, desired trajectory, desired planar cuts, etc. are stored in memory for retrieval during the procedure.

One or more boundaries used by the robotic system 10 could be defined by a navigation pointer 106 by touching anatomy of interest with the navigation pointer 106 and capturing associated points on the anatomy with the guidance station 20. For example, the navigation pointer 106 (FIGS. 1 and 4) could be used to outline the boundary. Additionally, or alternatively, the navigation pointer 106 could be used to delineate soft tissue or other sensitive anatomical structures to be avoided by the surgical tool 22. These points, for example, could be loaded into the robotic system 10 to adjust the tool path to be followed in the semi-autonomous mode so that the surgical tool 22 avoids these areas. Other methods could be used to delineate and/or define anatomy of interest, e.g., as being anatomy to be removed, anatomy to be avoided, etc.

A line haptic object LH (see FIG. 7) may be created and stored in the robotic system 10 to constrain movement of the surgical tool 22 to stay along the desired trajectory. The line haptic object LH may have a starting point SP, as described further below and a target point TP, which defines a desired depth of the drill or bur. A planar haptic object PH (see FIG. 5) may be created for constraining movement of the surgical tool 22 to stay along a desired plane. Other haptic object shapes, sizes, etc. are also contemplated, including those that define volumes of material to be removed to receive the components 102, 104, as described further below. It should also be appreciated that other forms of virtual objects, other than haptic objects, could be employed to establish boundaries for the surgical tool 22, wherein such boundaries may be represented on one or more of the displays 28, 29 to show the user when the working end of the surgical tool 22 is approaching, reaching, and/or exceeding such boundaries.

Figure 5:
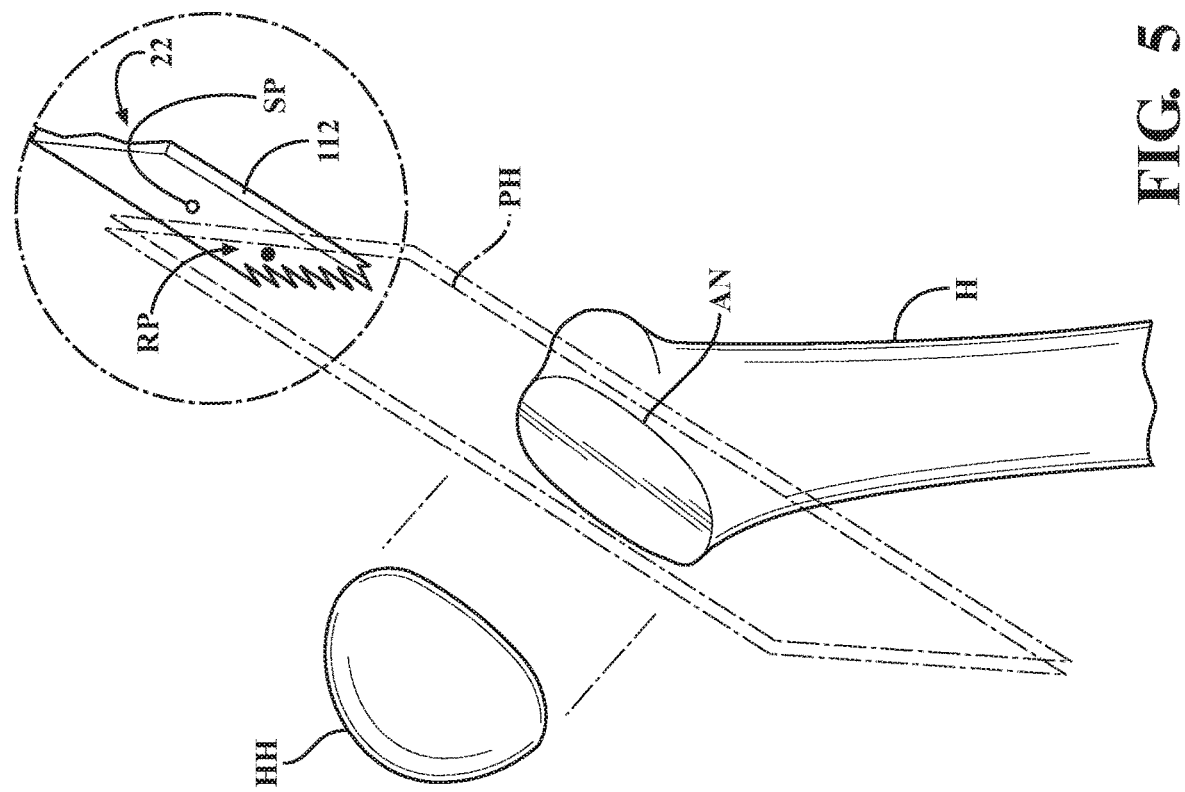
FIG. 5 is an illustration of a virtual object defining a resection plane for a humeral head of the humerus.
Figure 4:
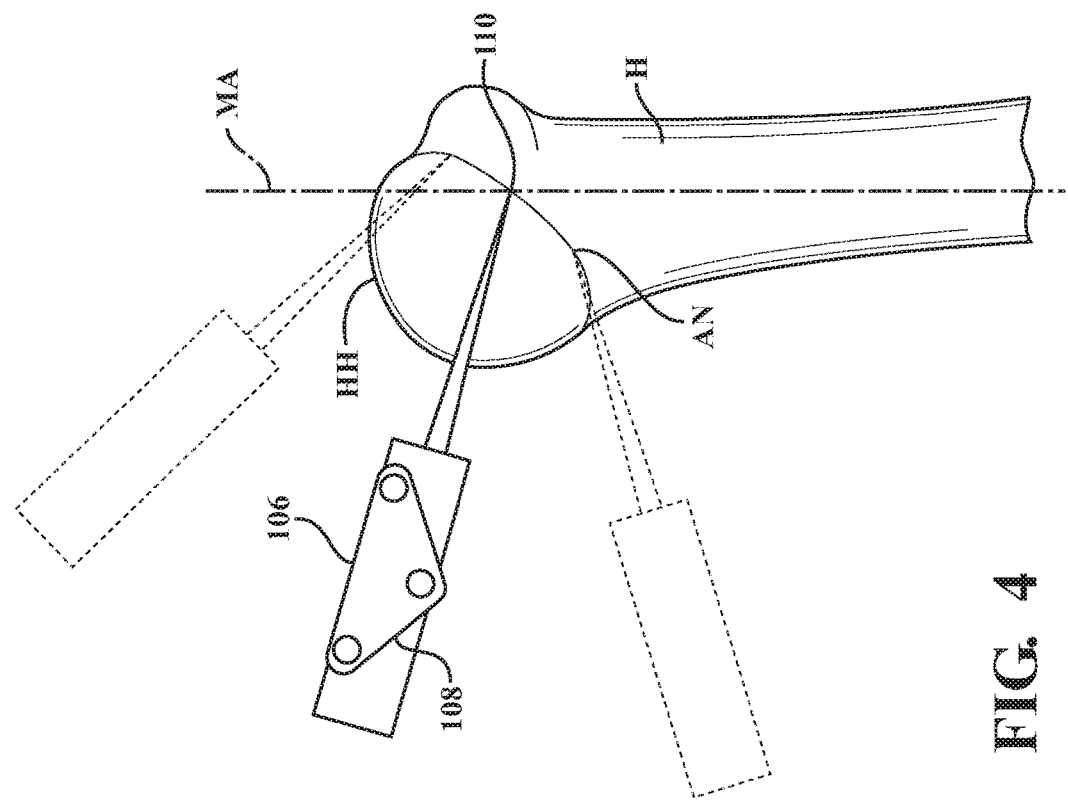
FIG. 4 is an illustration of a navigation pointer being used to locate landmarks on a humerus.

Referring to FIGS. 4 and 5, the humerus H is shown. The description that follows relates to preparation of the humerus H to receive the humeral component 102, but it should be appreciated that, during a surgical procedure, either of the humerus H or the glenoid cavity G may be prepared first to receive its associated implant component, or some combination of alternating preparation could be employed. The humerus H is prepared by first defining a resection plane along which a humeral head HH is to be resected from a remaining portion of the humerus H. This resection is planar in some embodiments, but may comprise a more complex surface topology in other embodiments. For example, the resection could provide a contoured surface, an undulating surface of ridges, or the like.

One of several options may be employed to determine the location of the resection of the humeral head HH, and by extension the location of the planar haptic object PH. In one case, a surgeon may prefer to make the resection along an anatomical neck AN. In this case, referring to FIG. 4, the surgeon may establish a virtual resection plane for the resection by using the navigation pointer 106, which comprises its own tracker 108 for purposes of determining a location of its tip 110. Navigation pointers 106 are used in registering pre-operative images or models to actual anatomy being treated during a surgical procedure. Here, the navigation pointer 106 may be used to register a pre-operative 3-D model (e.g., one generated from CT scan data, MRI data, or the like) of the humerus H to the actual humerus H and also to define the resection of the humeral head HH.

In order to define the resection of the humeral head HH, the user touches the tip 110 of the navigation pointer 106 to at least three locations along the anatomical neck AN, and the navigation controller 26 determines positions of these plurality of landmarks in a coordinate system registered to the humerus H (one or more coordinate systems may be employed). Once the positions of the landmarks are determined, the virtual resection plane can be defined as passing through each of the three points in the coordinate system. The location of the virtual resection plane defines a location of the planar haptic object PH shown in FIG. 5.

Other methods of establishing the resection includes placing the resection plane at a predetermined angle (e.g., 135 degrees or other angle) with respect to a longitudinal axis MA of the humerus (e.g. relative to an intramedullary axis of the intramedullary canal) defined in the coordinate system. Yet another method of establishing the plane comprises selecting one or more landmarks on the humerus H, e.g., the greater tuberosity, lesser tuberosity, bicipital groove, and defining the resection based on the one or more landmarks, either alone, or in conjunction with the intramedullary axis MA of the intramedullary canal and/or in conjunction with an extramedullary axis or axis based on an outer shape of the humerus H.

Figure 6:
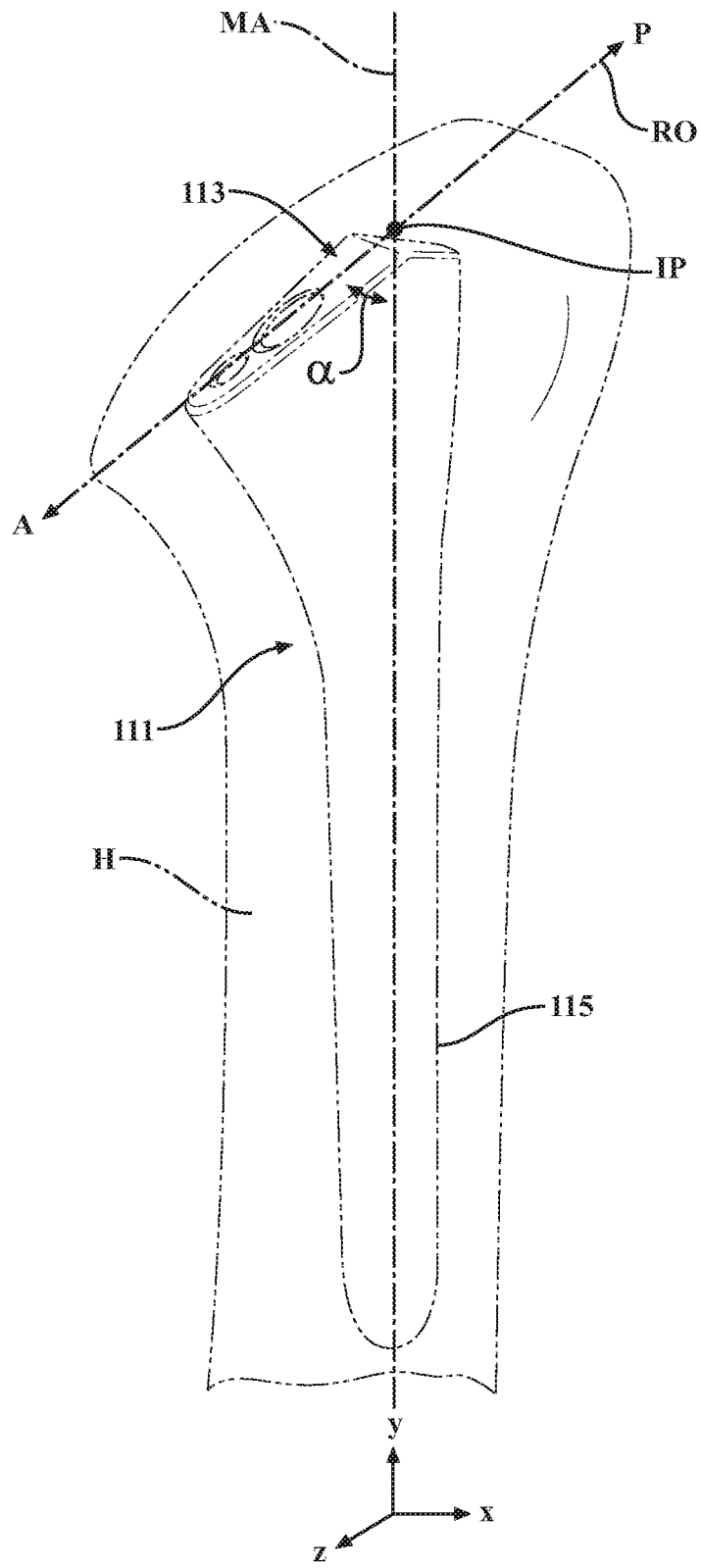
FIG. 6 is an illustration of a model of a stemmed implant component placed at a virtual location in the humerus to determine a location of the resection plane made in FIG. 5.
Figure 7:
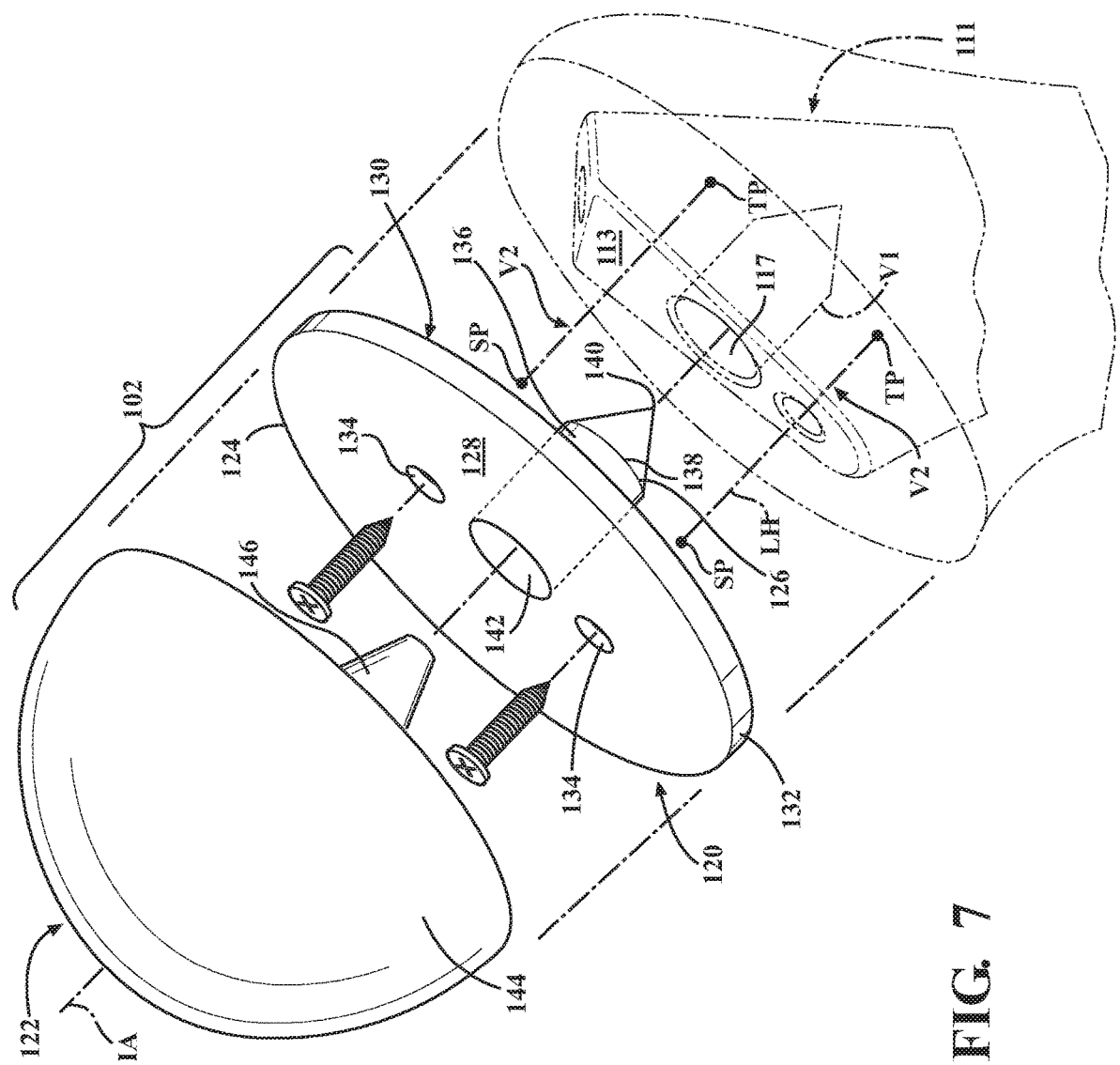
FIG. 7 is a close-up view of the model of the stemmed implant component at the virtual location in the humerus.
Figure 8:
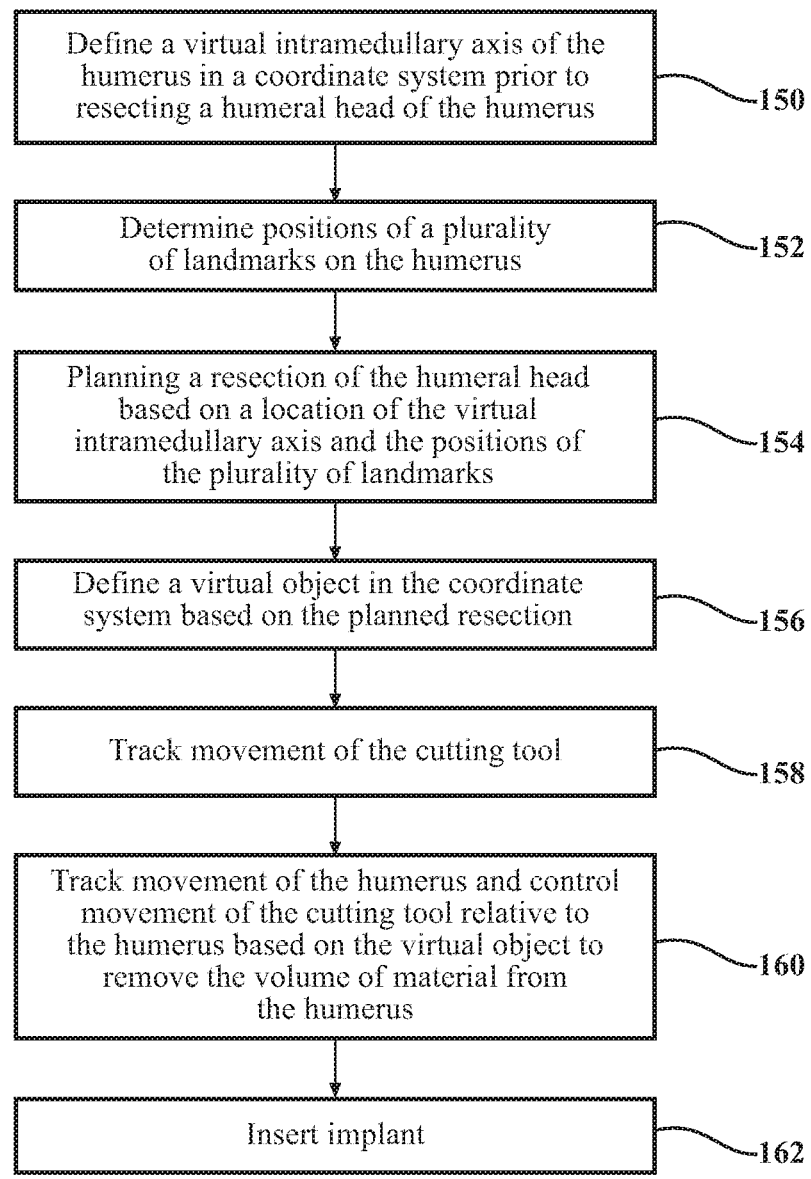
FIG. 8 is a flow diagram of steps taken in one method of planning the location of the resection plane.

Referring to FIGS. 6 through 8, another method of determining the location of the resection plane is shown. In this method, the resection plane is located based on a model of a stemmed implant component 111 so that if a revision surgery is necessary to remove the stemless humeral component 102 and replace it with the stemmed implant component 111, the amount of tissue (e.g., bone) that needs to be removed to accommodate the stemmed implant component 111 is minimized, i.e., the stemless humeral component 102 is located based on a virtual, future planned placement of the stemmed implant component 111 in the revision surgery. In essence, this provides a method for preparing the humerus H to receive the stemless humeral component 102 (also referred to as a stemless shoulder implant) based on a future location of the stemmed implant component 111 (also referred to as a stemmed shoulder implant) to be placed in the humerus H during a revision surgery. In one version, the future location of the stemmed implant component 111 is defined in the coordinate system associated with the humerus H prior to resecting the humeral head HH of the humerus H and prior to removing a volume of material from the humerus H to receive the stemless humeral component 102. The user, system, or a combination thereof, then plan a location of the stemless humeral component 102 in the coordinate system based on the future location of the stemmed implant component 111 in the manner described below so that movement of one or more cutting tools can be controlled to resect the humeral head HH and remove the volume of material from the humerus H to receive the stemless humeral component 102 based the planned location of the stemless humeral component 102, which is derived from a possible future location of the stemmed implant component 111.

Referring to FIG. 6, in this alternative method, a location of the intramedullary axis MA in the desired coordinate system is first determined. Since the humeral canal will remain substantially intact during the surgical procedure when placing the humeral component 102, the location of the intramedullary axis MA cannot be determined by simply placing a reamer or broach into the humeral canal. Instead, the intramedullary axis MA is determined virtually. For instance, pre-operative and/or intra-operative images (fluoroscopy, CT, MRI, ultrasound, etc.) and/or models (2-D or 3-D) can be used to determine the location of the intramedullary axis MA. In some cases, the surgeon or other user can locate the intramedullary axis MA in the desired coordinate system using one of the input devices of the guidance station 20 by placing a virtual line through the intramedullary axis MA on an image/model of the humerus H displayed on the displays 28, 29 similar to placing a line in a computer-aided design (CAD) software program. A-P and lateral views of the humerus H can be displayed to the user on the displays 28, 29, while the user employs the input device to add/move the virtual line through the viewed intramedullary axis MA to establish the location of the intramedullary axis MA in an image/model coordinate system. During registration, as described herein, the coordinates of the intramedullary axis MA in the image/model coordinate system are mapped to the actual humerus H so that movement of the intramedullary axis MA when the patient moves can be tracked by the guidance station 20. In other words, the location of the intramedullary axis MA is determined in the desired coordinate system, e.g., the model coordinate system or the coordinate system to which the pre-operative 3-D model of the humerus H is registered and in which the surgical tool 22 is being tracked relative to the 3-D model.

Other methods of determining the location of the intramedullary axis MA are also contemplated. For instance, the navigation pointer 106 could be employed to locate certain anatomical landmarks on the patient that have a predetermined relationship to the intramedullary axis MA. In one embodiment, the navigation pointer 106 may comprise a needle sharp pointer tip able to penetrate soft tissue to contact an exterior surface of the humerus H at one or more locations (e.g., 3 or more locations) on the humerus H with the navigation controller 26 using these points to automatically establish a virtual location of the intramedullary axis MA. Landmarks on both ends of the humerus H, or on only the humeral head HH, could be touched with the tip of the navigation pointer 106 to establish the intramedullary axis MA. In many cases, the virtual intramedullary axis of the humerus H is established prior to resecting the humeral head HH.

Once the location of the intramedullary axis MA is determined in the desired coordinate system, the ultimate virtual resection (e.g., the virtual resection plane) may be based on the plane defined by an upper surface 113 of the stemmed implant component 111. In other words, the user may first virtually plan the surgery by locating the stemmed implant component 111 at a desired future location (e.g., position and/or orientation should the stemmed implant component 111 need to be used in a future revision surgery) relative to the pre-operative model and the virtual intramedullary axis MA. The robotic system 10 could then derive the virtual resection as simply being the virtual plane passing through the upper surface 113 relative to the 3-D model. The robotic system 10 could then be programmed to resect the humeral head HH based on this virtual resection plane by controlling a sagittal saw blade 112 as described below.

In some cases, the surgeon or other user may require guidance as to where to locate the stemmed implant component 111 along the intramedullary axis MA. Such guidance may be established based on anatomical landmarks associated with the humeral head HH. In one embodiment, the user determines a location of a first virtual resection object RO in the desired coordinate system that intersects the virtual intramedullary axis MA to establish an intersection point IP. The first virtual resection object RO may comprise a line, plane, or other form of virtual object that is utilized to determine the location of the intersection point IP. The first virtual resection object RO may be defined by the user touching the tip 110 of the navigation pointer 106 to at least three locations along the anatomical neck AN. The navigation controller 26 then determines positions of these plurality of landmarks in the coordinate system registered to the humerus H. Once the positions of the landmarks are determined, a virtual plane can be defined as passing through each of the three points in the coordinate system. A line in the plane oriented in the A-P direction that intersects the intramedullary axis MA can then be defined as the first virtual resection object RO, as shown in FIG. 6. In this case, the intersection of the first virtual resection object RO with the virtual intramedullary axis MA establishes the intersection point IP.

With the intersection point IP established, the virtual resection can be defined by a virtual resection plane that passes through the intersection point IP, contains the first virtual resection object RO, and is orthogonal to the intramedullary axis MA in the A-P direction. However, this virtual resection plane may not be ideal for the stemmed implant component 111 owing to differences in the angle α of this virtual resection plane to the intramedullary axis MA and the angle of the upper surface 113 (and the associated upper surface plane) with respect to the intramedullary axis MA. In other words, if the stemmed implant component 111 is positioned with respect to the intramedullary axis MA so that a stem 115 of the stemmed implant component 111 lies along the intramedullary axis MA as needed to stay within the humeral canal and provide a stable fit therein, and the upper surface 113 in this position is unable to match the virtual resection plane that has been calculated, then the navigation controller 26 may adjust the virtual resection plane so that it matches the angle of the upper surface 113 or the navigation controller 26 may perform a best fit analysis of the two planes to create a new virtual resection plane. In this case, the navigation controller 26 may analyze the best fit adjustment of the location of the stemmed implant component 111 to ensure that the best fit does not virtually move the stem 115 outside of the humeral canal.

Once the resection location has been determined, the robotic system 10 stores the virtual resection object (e.g., the final virtual resection plane) to guide operation of the manipulator 56 and the surgical tool 22. As shown in FIG. 5, the surgical tool 22 comprises the sagittal saw blade 112. The virtual object, in this case the planar haptic object PH, is employed to constrain movement of the saw blade 112 so that the resection is made according to the surgeon's plan. This may include operating the manipulator 56 in the haptic mode and/or semi-autonomous mode to perform the resection. In the haptic mode, the user manually manipulates the surgical tool 22 while the manipulator 56 keeps the saw blade 112 confined within the planar haptic object PH via haptic feedback to the user.

Visual feedback can additionally be provided on the displays 28, 29, which depict a representation of the saw blade 112 and a representation of the humerus H and updates in substantially real-time such representations so that the user and/or others can visualize movement of the saw blade 112 relative to the humerus H during resection. The user operates the saw blade 112 to finish the resection and ready the humerus H for further preparation to receive the humeral component 102. In some versions, the humeral head HH is manually resected using a conventional sagittal saw outfitted with a separate navigation tracker so that the user can visualize a location of the saw blade 112 relative to the desired resection on the displays 28, 29 while manually resecting the humeral head HH.

In some embodiments, before sawing commences, the robotic system 10 autonomously aligns the saw blade 112 with the desired resection plane. Such autonomous positioning may be initiated by the user pulling a trigger (not shown) on the surgical tool 22, or otherwise providing input to the robotic system 10 to start the autonomous movement. In some cases, a reference point RP of the surgical tool 22 is first brought to within a predefined distance of a starting point SP of the planar haptic object PH (such as within a predefined starting sphere as shown or starting box). Once the reference point RP is within the predefined distance of the starting point SP, then pulling the trigger (or alternatively pressing a foot pedal or actuating some other input) causes the manipulator 56 to autonomously align and position the saw blade 112 on the desired plane. Once the saw blade 112 is in the desired pose, the robotic system 10 may effectively hold the surgical tool 22 on the desired plane (i.e., within the planar haptic object PH) by tracking movement of the patient and autonomously adjusting the manipulator 56 as needed to keep the saw blade 112 on the desired trajectory/plane.

While the robotic system 10 holds the saw blade 112 on the desired plane, the user may then manually manipulate the surgical tool 22 to move (or cause movement of) the saw blade 112 within the planar haptic object PH toward the bone to resect the humeral head HH. In some cases, such as in the haptic mode, the robotic system 10 constrains the user's movement of the surgical tool 22 to stay in the planar haptic object PH by providing haptic feedback to the user should the user attempt to move the surgical tool 22 in a manner that deviates from the planar haptic object PH and the desired plane. If the user desires to return the manipulator 56 to a free mode, for unconstrained movement of the surgical tool 22, the user can then pull the surgical tool 22 back along the planar haptic object PH, away from the patient, until an exit point of the planar haptic object PH is reached.

Once the humeral head HH has been resected, the humerus H is ready to be further prepared for receiving the humeral component 102 of the shoulder implant system 100. In some embodiments, one or more virtual objects that extend below the virtual resection plane could be used by the manipulator controller 54 to define a volume of material to be removed from the humerus H to receive the humeral component 102. The manipulator controller 54 is configured to operate the manipulator 56 to control movement of a drill, bur, saw blade, or other cutting tool, based on the one or more virtual objects. The one or more virtual objects may be sized so that a distal portion of the volume of material to be removed from the humerus H extends below the anatomical neck AN of the humerus and terminates above a diaphysis DPH of the humerus H (see FIG. 3) so that a substantial portion of a humeral canal remains intact after the humeral component 102 is fully seated in the humerus H.

Referring to FIG. 7, the stemmed implant component 111 has a bore 117 that defines a location for receiving a humeral head component (not shown). In order to take full advantage of planning the location of the humeral component 102 of the shoulder implant system 100 so that a minimum amount of tissue is removed in the event of a revision surgery to remove the humeral component 102 and replace it with the stemmed implant component 111, the location of any distal portion of the humeral component 102 that extends below the resection can be centered on the bore 117.

The humeral component 102 shown in FIG. 7 comprises a distal body 120 configured to be installed on the humerus H to receive a proximal body 122. The distal body 120 comprises a base flange 124 that can be installed on the resected surface of the humerus H, in a cavity below the surface, or the like. A central anchor 126 depends distally from the base flange 124. The base flange 124 may have a generally annular shape, although in other examples, the base flange 124 may have other shapes including oblong, cruciform, etc. The base flange 124 includes a proximal end surface 128, a distal bone-engaging surface 130, and a side base flange surface 132. Proximal end surface 128 may be flat as shown, but in other embodiments it may be inclined or sloped. Side base flange surface 132 may have a uniform height, the height measured from distal to proximal ends of side base flange surface 132, or the height may vary along proximal end surface 128. Distal bone-engaging surface 130 may include a porous surface, for example porous titanium alloy, across all or a portion of its surface to provide better fixation of the implanted distal body 120 with the bone.

Base flange 124 includes at least one hole 134 extending from proximal end surface 128 to distal bone-engaging surface 130. The holes 134 are each adapted to receive a screw. In the illustrated embodiment, there are two holes 134 and two screws, although there can be more or fewer holes and/or screws. The screws may be variable angle locking screws capable of being inserted through holes 134 at variable angles, with the heads of the screws having locking threads to mate with corresponding locking threads in the holes. The screws may engage the bone to provide fixation of the distal body 120 in the bone. The screws may have varying lengths to accommodate bone purchase to help with fixation, although any combination of screw lengths may be appropriate.

The central anchor 126 is coupled to the base flange 124 at a first end and extends distally from the base flange 124 along the implant axis IA to a second end. In the illustrated embodiment, the central anchor 126 has a straight portion 136, which may be cylindrical, and a tapered portion 138, which may be conical or frustoconical. Tapered portion 138 is tapered along the implant axis IA so that the proximal end of the tapered portion 138 has a relatively large diameter, with the diameter of the central anchor 126 generally narrowing toward second end until the central anchor terminates in distal tip 140.

The distal body 120 may further define an opening 142. Opening 142 may extend distally along the implant axis IA from proximal end surface 128 of base flange 124. Opening 142 may extend partially or fully through the central anchor 126 along the implant axis IA or it may be shallow and extend only into base flange 124. The proximal body 122 has a hemispherical head 144 to provide an articulation surface for interfacing with a mating glenoid implant component described further below. A taper 146 extends distally and centrally from the head 144 to be received in the opening 142. The taper 146 may be placed within opening 142 and attached thereto, for example by threads, a taper lock such as a Morse taper, or the like. The proximal body 122 may be attached by any known securement means including screw or friction fit. The distal body 120 may include additional holes for use with insertion/extraction tools and/or for accepting sutures.

During preparation of the humerus H, one virtual object V1 may be sized and shaped to correspond to the anchor 126 to define the volume of material to be removed from the humerus H to receive the central anchor 126. In order to take full advantage of planning the location of the humeral component 102 of the shoulder implant system 100 so that a minimum amount of tissue is removed in the event of a revision surgery to remove the humeral component 102 and replace it with the stemmed implant component 111, the location of the virtual object V1 can be centered on the bore 117 (i.e., the virtual location of the bore 117 in the model). This way, the only tissue removed is tissue that would need to be removed for the stemmed implant component 111 during the revision surgery.

One or more secondary virtual objects V2 may be sized and shaped to correspond to pilot holes to be placed in the humerus H for the one or more locking screws. The secondary virtual objects V2 may comprise trajectories, such as line haptic objects LH. The secondary virtual objects V2 can similarly be located to intersect with portions of the stemmed implant component 111 as shown in FIG. 7 so that the only tissue removed is tissue that would need to be removed for the stemmed implant component 111 during the revision surgery.

The one or more virtual objects are registered to the coordinate system to which the pre-operative model is registered (or are defined in the pre-operative model) to define one or more virtual cutting boundaries for the surgical tool 22 so that the user is limited from removing more material than needed to accurately position the humeral component 102 securely within the humerus H. As previously described, the manipulator 56 may be operated in the haptic mode during cutting to generate haptic feedback to the user based on a position of the surgical tool 22 relative to the virtual cutting boundaries. For example, the manipulator 56 may be controlled by the manipulator controller 54 to generate haptic feedback in response to the working end of the surgical tool 22 reaching or exceeding a virtual cutting boundary defined by the virtual objects.

Owing to the attachment of the tracker 44 to the humerus H, the location of the working end of the surgical tool 22 relative to the humerus H can be visualized on the displays 28, 29, along with a visualization of the virtual objects. For instance, isometric, side, top, cross-sectional, or other views of the humerus H may be displayed with graphical representations of the virtual objects overlaid on the representation of the humerus H. Similarly, a representation of the working end of the surgical tool 22 can be displayed in relation thereto and updated so that the user is able to visualize, in substantially real-time, a pose of the surgical tool 22 relative to the humerus H and the associated virtual cutting boundaries.

Referring to FIG. 8, a flow diagram is shown of steps carried out in one exemplary method described herein. In step 150, prior to resecting the humeral head HH, the virtual intramedullary axis MA of the humerus H is defined in the desired coordinate system. Once the virtual intramedullary axis MA is defined, the positions of the landmarks on the humerus H are determined in step 152 by the guidance station 20 using the navigation pointer 106 or any other suitable technique.

In step 154, the resection of the humeral head HH is planned based on the location of the virtual intramedullary axis MA and the positions of the landmarks. For instance, the landmarks are used to establish the virtual resection plane that defines the intersection point IP as previously discussed, and then the virtual resection plane is modified to match the upper surface 113 of the stemmed implant component 111. In some cases, these merely comprises modifying the plane to create a new virtual resection plane orthogonal to the intramedullary axis MA in the A-P direction and oriented at an angle α that matches the angle formed by the upper surface 113 of the stemmed implant component 111 and the intramedullary axis MA when the stem 115 of the stemmed implant component 111 is properly aligned with the intramedullary axis MA. In some cases, the new virtual resection plane may also be constrained to pass through the same intersection point IP. The new virtual resection plane is defined in the desired coordinate system to control operation of the manipulator 54 and movement of a cutting tool, such as the saw blade 112 to resect the humeral head HH from the rest of the humerus H.

In step 156, one or more virtual objects V1, V2 are defined in the desired coordinate system to control operation of the manipulator 54 and movement of a cutting tool, such as a bur to remove material from the humerus H to receive an implant, such as the distal body 120 of the humeral component 102. In steps 158 and 160, the cutting tool is tracked relative to movement of the humerus H. At the same time, the virtual objects V1, V2 define boundaries that constrain movement of the cutting tool relative to the humerus H. The manipulator 54 can then be operated in one or more of the modes described herein to remove tissue from the humerus H to receive the distal body 120 in step 162.

Referring to FIGS. 9 through 14, preparation of the glenoid cavity G is illustrated. Preparation of the glenoid cavity G may comprise a combination of manual and robotic operations such as drilling, reaming, burring, and the like. As previously described, glenoid preparation can be done at any time in the procedure, and can be done immediately following humeral head HH resection, but before placement of the humeral component 102, after placement of the humeral component 102, or before preparation of the humerus H. In FIGS. 9 and 10, a retractor 199 is used to retract the humerus H and expose the glenoid cavity G.

Figure 11:
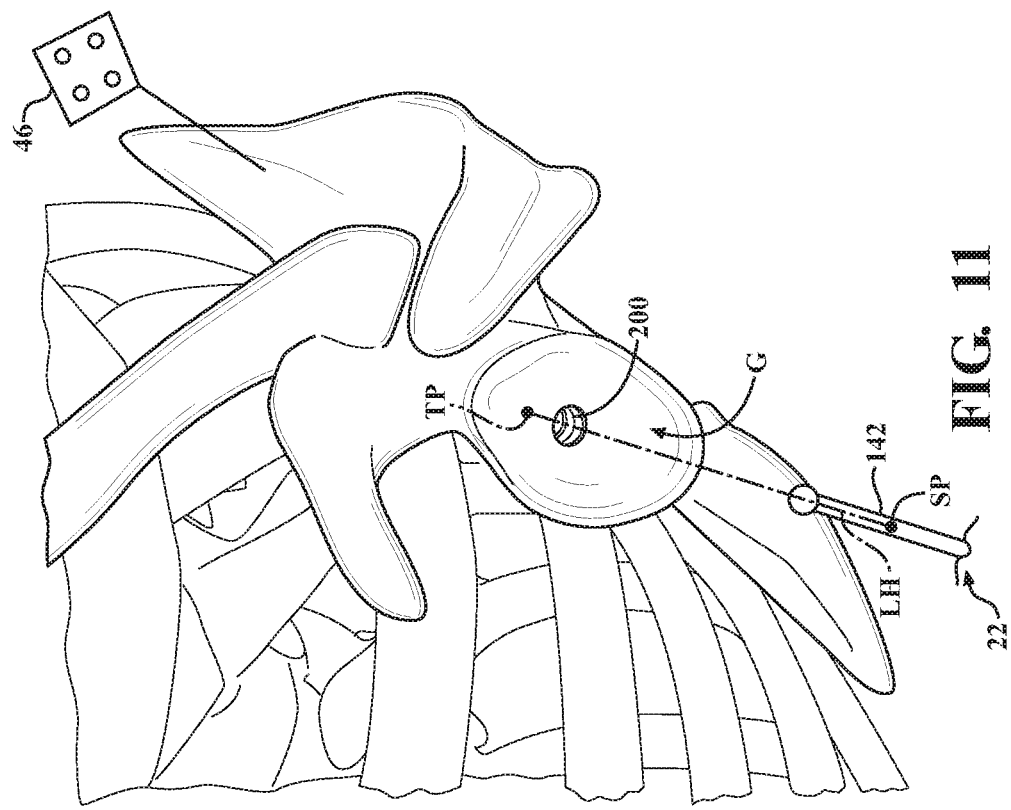

Referring to FIG. 11, a center hole 200 is first prepared through the glenoid cavity G. The center hole 200 may be defined by a virtual object, such as a line haptic object LH that defines the trajectory and stopping location for the center hole 200. A bur, drill or other accessory may be used in the surgical tool 22 to form the center hole 200 in the free mode (using visualization of the desired trajectory and depth as a guide), in the haptic mode (using haptic feedback to keep the surgical tool 22 on the trajectory and at a suitable depth), or in the semi-autonomous mode in which the manipulator 56 moves the surgical tool 22 autonomously along the trajectory to prepare the center hole 200 at the desired depth.

Owing to the attachment of the tracker 46 to the scapula S, the location of the working end of the surgical tool 22 relative to the glenoid cavity G can be visualized on the displays 28, 29, along with a visualization of the virtual object, such as the line haptic object LH. For instance, isometric, side, top, cross-sectional, or other views of a representation of the glenoid cavity G may be displayed with virtual representations of the line haptic object LH overlaid on the representation of the glenoid cavity G. Similarly, a representation of the working end of the surgical tool 22 can be displayed in relation thereto and updated so that the user is able to visualize, in substantially real-time, a pose of the surgical tool 22 relative to the glenoid cavity G and the associated virtual line haptic object LH, which also defines a virtual cutting boundary for the surgical tool 22.

Figure 12:
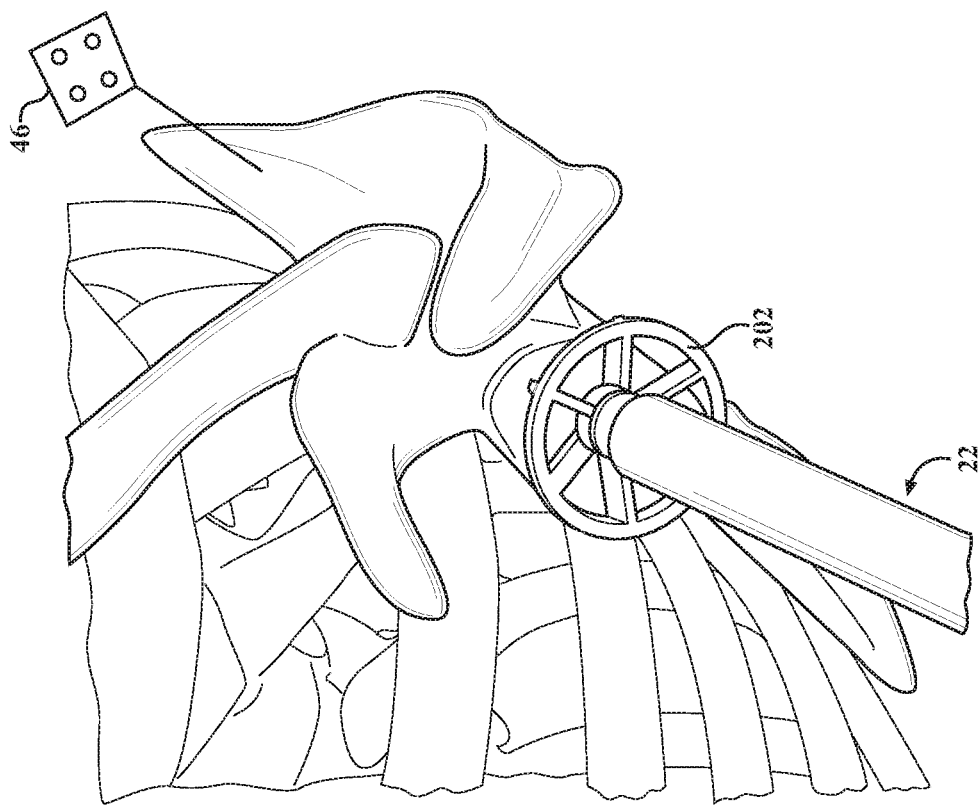

Referring to FIG. 12, once the center hole 200 is prepared, an appropriately sized reamer head 202 can be used on the surgical tool 22 to contour the glenoid cavity G to provide a desired contoured surface for receiving the glenoid component 104. The reamer head 202 has a distally protruding centering pin (not shown) that is seated in the center hole 200 to center the reamer head 202 and at least partially orient the reamer head 202 during reaming operations. Another virtual object may also be associated with the desired contoured surface of the glenoid cavity G so that the reamer head 202 is limited from penetrating beyond the desired contoured surface. As a result, in some versions, the center hole 200 may not be needed to locate the centering pin of the reamer head 202 as the manipulator 56 controls the location of the reamer head 202 based on the associated contoured surface virtual object. In some embodiments, a bur is used to shape/contour the glenoid cavity G to receive the glenoid component 104.

Figure 13:
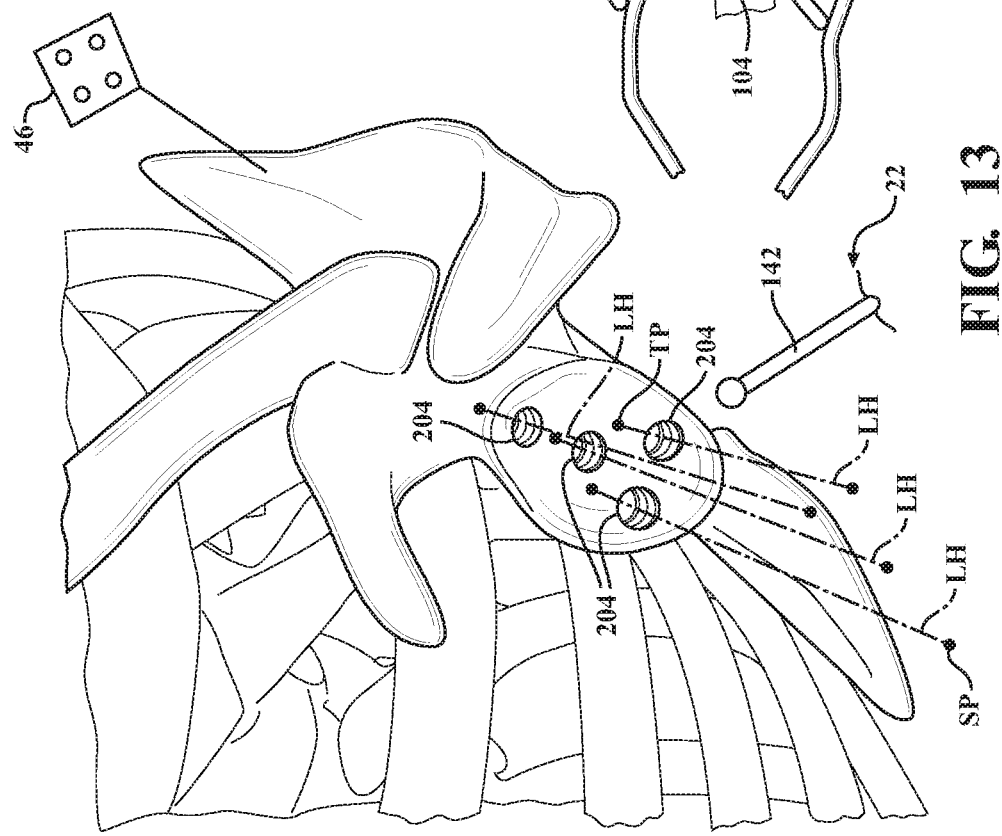

Referring to FIG. 13, peg holes 204 can be formed through the glenoid cavity G similar to the center hole 200. Each of the peg holes 204 may be defined by a virtual object, such as a line haptic object LH that defines the trajectory and stopping location for the peg hole 204. A bur, drill or other accessory may be used in the surgical tool 22 to form the peg holes 204 in the free mode (using visualization of the desired trajectory and depth as a guide), in the haptic mode (using haptic feedback to keep the surgical tool 22 on the trajectory and at a suitable depth), or in the semi-autonomous mode in which the manipulator 56 moves the surgical tool 22 autonomously along the trajectory to prepare the peg holes 204 at the desired depths. In some embodiments, one or more of the virtual objects may be active at a given time, inactive, or combinations thereof. For example, when preparing the peg holes 204, multiple, separate line haptic objects LH defining the desired trajectories are employed, but only one or more of them may be active at any given time so that the user and/or the manipulator 56 is able to focus on preparing one peg hole at a time. With only one line haptic object LH being active, then the manipulator 56 is able to lock the surgical tool 22 on that line haptic object LH without inadvertently locking onto a different, adjacent line haptic object. The user can also manually select, via the user interface for the navigation controller 26, which peg hole is to be prepared and the robotic system 10 can activate the associated line haptic object LH accordingly.

Figure 14:
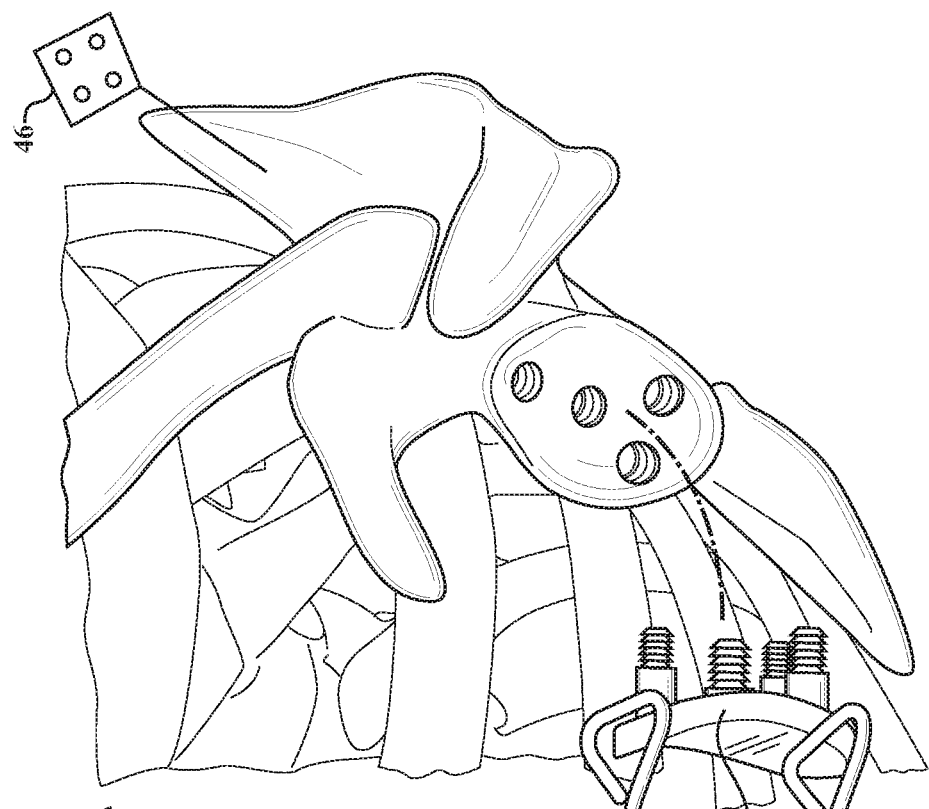

Referring to FIG. 14, once the peg holes 204 are formed, the glenoid component 104 can be placed in the glenoid cavity G and secured by press-fit, bone cement or other adhesive, screws, or otherwise.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A method for performing robotic surgery with a robotic manipulator and a cutting tool coupled to the robotic manipulator to prepare a humerus to receive a shoulder implant, the method comprising the steps of:
    determining positions of a plurality of landmarks on the humerus;
    defining a virtual resection in a coordinate system based on the positions of the plurality of landmarks;
    defining a virtual object in the coordinate system based on a location of the virtual resection wherein the virtual object defines a volume of material to be removed from the humerus to receive the shoulder implant;
    tracking movement of the cutting tool;
    tracking movement of the humerus; and
    controlling movement of the cutting tool relative to the humerus based on the virtual object to remove the volume of material from the humerus.

2. The method of claim 1, wherein the virtual object is sized so that a distal portion of the volume of material to be removed from the humerus extends below an anatomical neck of the humerus and terminates above a diaphysis of the humerus so that a substantial portion of a humeral canal of the humerus remains intact after the shoulder implant is seated in the humerus.

3. The method of claim 1, wherein the virtual object comprises a virtual cutting boundary.

4. The method of claim 3, comprising generating haptic feedback to the user based on a position of the cutting tool relative to the virtual cutting boundary.

5. The method of claim 3, comprising controlling movement of the cutting tool in a haptic mode of the robotic manipulator in which a user manually manipulates the cutting tool and the robotic manipulator generates haptic feedback in response to the cutting tool reaching or exceeding the virtual cutting boundary.

6. The method of claim 3, comprising controlling movement of the cutting tool in a free mode of the robotic manipulator in which a user is allowed to freely manipulate the cutting tool beyond the virtual cutting boundary.

7. The method of claim 1, comprising controlling movement of the cutting tool in an autonomous mode of the robotic manipulator to control movement of the cutting tool autonomously along a tool path.

8. A method for performing robotic surgery with a robotic manipulator and a cutting tool coupled to the robotic manipulator to prepare a humerus to receive a shoulder implant, the method comprising the steps of:

defining a virtual intramedullary axis of the humerus in a coordinate system prior to resecting a humeral head of the humerus;

determining positions of a plurality of landmarks on the humerus;

planning a resection of the humeral head based on a location of the virtual intramedullary axis and the positions of the plurality of landmarks;

defining a virtual object in the coordinate system based on the planned resection, wherein the virtual object defines a volume of material to be removed from the humerus to receive the shoulder implant;

tracking movement of the cutting tool;

tracking movement of the humerus; and controlling movement of the cutting tool relative to the humerus based on the virtual object to remove the volume of material from the humerus.

9. The method of claim 8, wherein planning the resection of the humeral head based on the location of the virtual intramedullary axis and the positions of the plurality of landmarks further comprises planning the resection of the humeral head based on a future location of a stemmed shoulder implant with respect to the coordinate system.

10. The method of claim 9, wherein defining the virtual object in the coordinate system based on the planned resection further comprises defining the location of the virtual object in the coordinate system based on the future location of the stemmed shoulder implant with respect to the coordinate system.

11. A method for planning a surgery with a robotic surgery system to prepare a humerus to receive a stemless shoulder implant based on a future location of a stemmed shoulder implant to be placed in the humerus during a revision surgery, the robotic surgery system comprising a robotic manipulator, a localizer configured to track movement of the robotic manipulator, and a controller coupled to the robotic manipulator and the localizer, the method comprising the steps of:

defining, with the controller, the future location of the stemmed shoulder implant in a coordinate system associated with the humerus, wherein the future location is defined in the coordinate system prior to resecting a humeral head of the humerus and prior to removing a volume of material from the humerus to receive the stemless shoulder implant; and planning, with the controller, a location of the stemless shoulder implant in the coordinate system based on the future location of the stemmed shoulder implant defined in the coordinate system so that movement of one or more cutting tools can be controlled to resect the humeral head and remove the volume of material from the humerus to receive the stemless shoulder implant based on the planned location of the stemless shoulder implant, which is derived from the future location of the stemmed shoulder implant.

12. The method of claim 11, wherein defining, with the controller, the future location of the stemmed shoulder implant in the coordinate system comprises:

defining, with the controller, a virtual intramedullary axis of the humerus in the coordinate system; and determining, with the controller, positions of a plurality of landmarks on the humerus.

13. The method of claim 12, wherein planning, with the controller, the location of the stemless shoulder implant in the coordinate system comprises:

planning with the controller, a resection of the humeral head based on a location of the virtual intramedullary axis and the positions of the plurality of landmarks; and defining, with the controller, a volume of material to be removed from the humerus receive the stemless shoulder implant, wherein the volume of material is defined in the coordinate system.

14. The method of claim 13, wherein defining, with the controller, the volume of material to be removed from the humerus comprises defining, with the controller, the volume of material to be removed that so that a distal portion of the volume of material to be removed from the humerus extends below an anatomical neck of the humerus and terminates above a diaphysis of the humerus.

15. The method of claim 13, wherein defining, with the controller, the volume of material to be removed from the humerus comprises defining, with the controller, a virtual object in the coordinate system, wherein the one or more cutting tools are controlled based on the virtual object.

16. The method of claim 15, wherein the virtual object comprises a virtual cutting boundary.

* * * * *